United States Patent
Boase et al.

(10) Patent No.: US 7,022,724 B2
(45) Date of Patent: Apr. 4, 2006

(54) COGNITION ENHANCING DERIVATIVES OF ISOXAZOLE TRIAZOLOINDANE GABA-A α5 RECEPTOR SUBUNIT LIGANDS

(75) Inventors: Amanda Louise Boase, London (GB); Tamara Ladduwahetty, London (GB); Angus Murray MacLeod, Bishops Stortford (GB); Kevin John Merchant, Ware (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 131 days.

(21) Appl. No.: 10/277,450

(22) Filed: Oct. 22, 2002

(65) Prior Publication Data

US 2004/0058970 A1 Mar. 25, 2004

(30) Foreign Application Priority Data

Oct. 18, 2001 (GB) .................................. 0125086

(51) Int. Cl.
*A61K 31/422* (2006.01)
*C07D 487/04* (2006.01)

(52) U.S. Cl. ...................................... 514/378; 548/240

(58) Field of Classification Search ................ 548/240; 514/378
See application file for complete search history.

(56) References Cited

OTHER PUBLICATIONS

Voitenko et al., Triazolo and tetrazoloisoindoles., Chemistry of Heterocyclic Compounds, 38(9), Sep. 2002, pp. 1019-1039.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*

* cited by examiner

*Primary Examiner*—Kamal A. Saeed
*Assistant Examiner*—Rebecca Anderson
(74) *Attorney, Agent, or Firm*—John C. Todaro; Melvin Winokur

(57) ABSTRACT

The present invention relates to compounds of formula I:

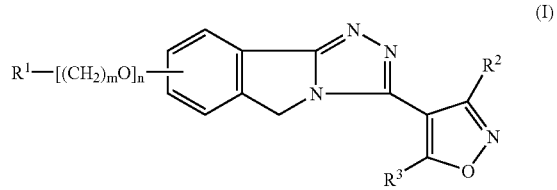

in which $R^1$ is a linear group or a five membered heterocycle optionally fused to a phenyl ring, $R^2$ is a 5-membered heterocycle, $R^3$ is chosen from a range of substituents, m is 0–3 and n is 0 or 1; the compounds are generally inverse agonists at GABA-A receptors containing the alpha 5 subunit and so are useful in methods of enhancing cognition in subjects with diminished cognition in diseases such as Alzheimer's Disease.

7 Claims, No Drawings

COGNITION ENHANCING DERIVATIVES OF ISOXAZOLE TRIAZOLOINDANE GABA-A α5 RECEPTOR SUBUNIT LIGANDS

The present invention relates to a class of substituted isoxazole triazoloindane derivatives and to their use in therapy. More particularly, this invention is concerned with substituted isoxazole triazoloindane derivatives which are ligands for $GABA_A$ receptors containing the α5 subunit and are therefore useful in therapy where cognition enhancement is required.

Receptors for the major inhibitory neurotransmitter, gamma-aminobutyric acid (GABA), are divided into two main classes: (1) $GABA_A$ receptors, which are members of the ligand gated ion channel superfamily; and (2) $GABA_B$ receptors, which maybe members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangements of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βγδ, α4βδ. Subtype assemblies containing an α subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radio ligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108 that benzodiazepine receptor inverse agonist, β-CCM enhanced spatial learning in the Morris watermaze. However, β-CCM and other conventional benzodiazepine agonists are proconvulsant, which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that an α5 receptor partial or full inverse agonist, which is relatively free of activity at α1 and/or α2 and/or α3 receptor binding sites, can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α, α2 and α3 receptor binding sites are preferred.

WO-A-9850385 discloses substituted 1,2,4-triazolo[3,4-a]pyridazines which are $GABA_A$ receptor ligands selective for the α5 binding sites.

WO-A-9917769 discloses substituted indeno[1,2-c]-, naphtho[1,2-c]- and benzo[6,7]cyclohepta[1,2-c]pyrazoles as tyrosine kinase inhibitors.

The present invention provides compounds of formula I:

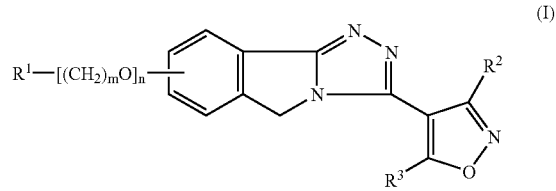

in which:

$R^1$ is (i) hydrogen, halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy$C_{1-6}$alkyl, $C_{1-6}$alkoxy$C_{1-6}$alkyl, amino$C_{1-6}$alkyl or $C_{1-6}$alkylcarbonyl each of which is unsubstituted or substituted by one, two or three halogen atoms;

(ii) a 5-membered heterocyclic ring containing 1, 2, 3 or 4 heteroatoms independently selected from O, N or S, at most one being oxygen or sulphur, or a 6-membered aromatic ring optionally containing 1 or 2 nitrogen heteroatoms, said rings being unsubstituted or substituted by at least one halogen, hydroxy, COOH, cyano, $NR^aR^b$, $CONR^aR^b$, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, $C_{1-6}$alkoxy$C_{1-6}$alkyl, hydroxy$C_{1-6}$alkyl, amino$C_{1-6}$alkyl or $C_{1-6}$alkylcarbonyl, each of which is itself unsubstituted or substituted by one, two or three halogen atoms; or (iii) a 5-membered heterocyclic ring containing 1, 2, 3 or 4 heteroatoms independently selected from O, N or S, at most one being oxygen or sulphur, or a 6-membered aromatic ring optionally containing 1 or 2 nitrogen heteroatoms, one of said rings being fused with a phenyl ring wherein the resulting ring system is unsubstituted or substituted with at least one group selected from halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy$C_{1-6}$alkyl, $C_{1-6}$alkoxy$C_{1-6}$alkyl, amino$C_{1-6}$alkyl or $C_{1-6}$alkylcarbonyl each of which is unsubstituted or substituted by one, two or three halogen atoms;

$R^2$ is a 5-membered heterocyclic ring containing 1, 2, 3 or 4 heteroatoms independently selected from O, N or S, at most one being oxygen or sulphur, or a 6-membered aromatic ring optionally containing 1 or 2 nitrogen heteroatoms, which ring is unsubstituted or substituted with at least one group selected from halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy$C_{1-6}$alkyl, $C_{1-6}$alkoxy$C_{1-6}$alkyl, amino$C_{1-6}$alkyl or $C_{1-6}$alkylcarbonyl each of which is itself unsubstituted or substituted by one, two or three halogen atoms;

$R^3$ is hydrogen, halogen, cyano, armino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy$C_{1-6}$alkyl, $C_{1-6}$alkoxy$C_{1-6}$alkyl, amino$C_{1-6}$alkyl, $C_{1-6}$alkylcarbonyl or $NR^cR^d$, each of which is unsubstituted or substituted by one, two or three halogen atoms;

$R^a$ and $R^b$ are each independently hydrogen, $C_{1-6}$alkyl, $C_{1-6}$alkoxy, $C_{2-6}$alkenyl, $C_{2-6}$alkynyl, amino$C_{1-6}$alkyl or phenyl;

$R^c$ and $R^d$ are each independently hydrogen, $C_{1-6}$alkyl, $C_{1-6}$alkoxy, $C_{2-6}$alkenyl, $C_{2-6}$alkynyl or $C_{1-4}$alkyl substituted by a 6-membered heterocyclic group containing 1 or 2 nitrogen atoms;

m is 0, 1, 2 or 3; and n is 0 or 1;

and pharmaceutically acceptable salts thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "hydroxy$C_{1-6}$alkyl", "$C_{1-6}$alkylcarbonyl", and "amino$C_{1-6}$alkyl" are to be construed in an analogous manner.

Unless otherwise specified, 5- and 6-membered heterocyclic rings containing 1, 2 or 3 nitrogen heteroatoms or 1 oxygen or 1 sulphur heteroatom shall include pyridinyl, pyridazinyl, pyrmidinyl, pyrazinyl, pyrrolyl, furyl, thienyl, pyiazolyl, oxazolyl, isoxazolyl, thiazolyl, isothiazolyl, imidazolyl, oxadiazolyl, thiadiazolyl and triazolyl groups. Suitable 6-membered heterocyclic rings containing 3 nitrogen atoms include 1,2,4-triazine and 1,3,5-triazine. A suitable heterocyclic ring containing 4 nitrogen atoms is the tetrazole ring. When a heterocyclic ring comprises a hydroxy group as a susbstituent, and keto-enol tautomerism is possible, both tautomers are included within the scope of the invention.

The expression "6-membered aromatic ring" will, unless otherwise specified, include phenyl.

The term "halogen" as used herein included fluorine, chlorine, bromine and iodine.

As used herein the term "$C_{1-6}$alkoxy" includes methoxy and ethoxy groups, and straight-chained and branched propoxy, butoxy, pentoxy and hexoxy groups. Derived expressions such as "$C_{2-6}$alkenyloxy", "$C_{2-6}$alkynyloxy" and "$C_{1-6}$alkoxy$C_{1-6}$alkyl" should be construed in an analogous manner.

In the compounds of formula (I), $R^1$ is typically (i) hydrogen, halogen, hydroxy, cyano, nitro, $C_{1-4}$alkyl, $C_{1-4}$alkoxy or halogenated $C_{1-4}$alkoxy; preferably hydrogen, bromo, nitro, cyano, hydroxy, methyl, methoxy or trifluoromethoxy; (ii) a phenyl group, a phenyl group substituted by nitro, cyano, halogen, $C_{1-4}$alkyl or halogenated $C_{1-4}$alkyl; a 5-membered heterocyclic group containing either one oxygen heteroatom, one sulphur heteroatom, from 1 to 3 nitrogen heteroatoms or one nitrogen and one sulphur or oxygen heteroatom, the heterocyclic group being either unsubstituted or substituted with, for example, nitro, $C_{1-4}$alkyl or $C_{1-4}$alkoxy$C_{1-4}$alkyl; or a 6-membered heterocyclic group containing 1 or 2 nitrogen heteroatoms and being unsubstituted or substituted with halogen, $NR^aR^b$, $CONR^aR^b$, $C_{1-4}$alkyl, $C_{1-4}$alkoxy or halogenated $C_{1-4}$alkyl, wherein $R^a$ and $R^b$ are as defined above. We generally prefer, under this definition that $R^1$ is a phenyl group, a phenyl group substituted with cyano, or a pyridine, pyrimidine, pyradizine, pyrazine, tetrahydropyridine, furan, thiazole or triazole ring, the ring being unsubstituted or substituted by at least one $NR^aR^b$, $CONR^aR^b$, methyl, cyano, COOH, methoxy or pyrazinyl group. In the third alternative, $R^1$ may be a 5- or 6-membered heterocyclic ring fused with a phenyl ring. The resulting ring system may be unsubstituted or substituted by a variety of substitutents. Of these substituents we generally prefer the $C_{1-4}$alkyl or halogenated $C_{1-4}$alkyl and most prefer the trifluoromethyl substituent. The ring system itself is typically composed of a phenyl ring fused with either a furyl ring, a thienyl ring or a pyridine ring.

In the compounds of the present invention, $R^2$ is generally a phenyl ring, a 5-membered heterocyclic ring or a 6-membered heterocyclic ring as hereinabove defined. These rings may be unsubstituted or substituted by a variety of substituents. We generally prefer that $R^2$ represents a phenyl ring, either unsubstituted or substituted, preferably unsubstituted. When substituted this is preferably by a halogen atom and is most preferably the 4-fluorophenyl group.

The present invention provides compounds of formula (I) in which $R^3$ may be a variety of substituents. We generally prefer that $R^3$ represents a halogen, $C_{1-4}$alkyl, hydroxy$C_{1-4}$alkyl, halogenated $C_{1-4}$alkyl or $NR^cR^d$ group, in which $R^c$ and $R^d$ are as defined above, more preferably a halogen, $C_{1-2}$alkyl, hydroxy$C_{1-2}$alkyl, halogenated $C_{1-2}$alkyl or $NHR^d$ group, in which $R^d$ is as defined above, and most preferably a chloro, methyl, hydroxymethyl, fluoromethyl or

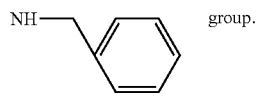

group.

In a preferred embodiment of the present invention we provide compounds of formula (I), as shown above, in which:

n represents 0 and $R^1$ represents hydrogen, cyano, amino, bromo, methyl, methoxy, phenyl, cyanophenyl, pyridinyl, pyrimidinyl, pyridazinyl, pyrazinyl, thiazolyl, furyl, tetrahydropyridin-4-yl, methylpyridazinyl, methoxypyridazinyl, aminopyridazinyl, 2-amino-3-methylpyridyl, aminocarbonylpyridinyl, methylpyrazinyl, carboxypyrazinyl, 4-methyl- 3,4,5,6-tetrahydro2H-[1,2']bipyrazinyl-6yl, dimethoxypyrimidinyl or N,N,N'-trimethyl-N'-pyridazin-3-ylethane-1,2-diamine; or n represents 1, m represents 2 and R¹ represents pyridinyl; R² represents phenyl or fluorophenyl;

R³ represents chloro, methyl, hydroxymethyl, fluoromethyl or

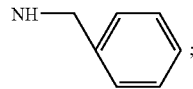

and pharmaceutically acceptable salts thereof.

Representative of the present invention are the following compounds:

3-(5-methyl-3-phenylisoxazol-4-yl)-5H-[1,2,4]triazolo[3,4-α]isoindole;
8-methoxy-3-(5-methyl-3-phenylisoxazol-4-yl)-5H-[1,2,4]triazolo[3,4-a]isoindole;
3-(5-methyl-3-phenylisoxazol-4-yl)-8-(1-methyl-1H-[1,2,4]triazol-3-ylmethoxy)-5H-[1,2,4]triazolo[3,4-a]isoindole;
8-bromo-3-(5-methyl-3-phenylisoxazol-4-yl)-5H-[1,2,4]triazolo[3,4-a]isoindole;
6-bromo-3-(5-methyl-3-phenylisoxazol-4-yl)-5H-[1,2,4]triazolo[3,4-a]isoindole;
8-(4,5-dihydro-1H-imidazol-2-yl)-3-(5-methyl-3-phenylisoxazol-4-yl)-5H-[1,2,4]triazolo[3,4-a]isoindole;
3-(5-methyl-3-phenylisoxazol-4-yl)-8-pyridin-2-yl-5H-[1,2,4]triazolo[3,4-α]isoindole;
3-(5-methyl-3-phenylisoxazol-4-yl)-8-pyrimidin-5-yl-5H-[1,2,4]triazolo [3,4-α]isoindole;
3-(5-methyl-3-phenylisoxazol-4-yl)-8-(6-methyl-pyridazin-3-yl)-5H-[1,2,4]triazolo[3,4-α]isoindole;
3-(5-methyl-3-phenylisoxazol-4-yl)-8-pyrimidin-2-yl-5H-[1,2,4]triazolo[3,4-α]isoindole;
3-(5-methyl-3-phenylisoxazol-4-yl)-8-thiazol-2-yl-5H-[1,2,4]triazolo[3,4-α]isoindole;
3-methyl-5-[3-(5-methyl-3-phenylisoxazol-4-yl)-5H-[1,2,4]triazolo[3,4-α]isoindol-8-yl]pyridin-2-ylamine;
5-[3-(5-methyl-3-phenylisoxazol-4-yl)-5H-[1,2,4]triazolo[3,4-α]isoindol-8-yl]-nicotinamide;
8-isothiazol-5-yl-3-(5-methyl-3-phenylisoxazol-4-yl)-5H-[1,2,4]triazolo[3,4-α]isoindole;
3-(5-methyl-3-phenylisoxazol-4-yl)-8-thiazol-4-yl-5H-[1,2,4]triazolo[3,4-α]isoindole;
3-(5-methyl-3-phenylisoxazol-4-yl)-8-pyrazin-2-yl-5H-[1,2,4]triazolo[3,4-α]isoindole;
8-(2,6-dimethoxypyrimidin-4-yl)-3-(5-methyl-3-phenylisoxazol-4-yl)-5H-[1,2,4]triazolo[3,4-α]isoindole;
8-(6-methoxypyridazin-3-yl)-3-(5-methyl-3-phenylisoxazol-4-yl)-5H-[1,2,4]triazolo[3,4-α]isoindole;
8-furan-3-yl-3-(5-methyl-3-phenylisoxazol-4-yl)-5H-[1,2,4]triazolo[3,4-α]isoindole;
6-[3-(5-methyl-3-phenylisoxazol-4-yl)-5H-[1,2,4]triazolo[3,4-α]isoindol-8-yl]-pyridazin-3-ylamine;
3-(5-methyl-3-phenylisoxazol-4-yl)-8-(2-methylpyridin-4-yl)-5H-[1,2,4]triazolo[3,4-α]isoindole;
3-(5-methyl-3-phenylisoxazol-4-yl)-8-(2-methylpyridin-3-yl)-5H-[1,2,4]triazolo[3,4-α]isoindole;
3-(5-methyl-3-phenylisoxazol-4-yl)-8-(6-methylpyrazin-2-yl)-5H-[1,2,4]triazolo[3,4-α]isoindole;
methyl-{6-[3-(5-methyl-3-phenylisoxazol-4-yl)-5H-[1,2,4]triazolo[3,4-α]isoindol-8-yl]pyridazin-3-yl}amine;
N,N,N'-trimethyl-N'-{6-[3-(5-methyl-3-phenylisoxazol-4-yl)-5H-[1,2,4]triazolo[3,4-α]isoindol-8-yl]pyridazin-3-yl}ethane-1,2-diamine;
3-(5-methyl-3-phenylisoxazol-4-yl)-8-(6-methylpyridin-2-yl)-5H-[1,2,4]triazolo[3,4-α]isoindole;
3-(5-methyl-3-phenylisoxazol-4-yl)-8-(4-methyl-3,4,5,6-tetrahydro-2H-[1,2']bipyrazinyl-6-yl)-5H-[1,2,4]triazolo[3,4-α]isoindole;
3-(5-methyl-3-phenylisoxazol-4-yl)-8-(5-methylpyridin-2-yl)-5H-[1,2,4]triazolo[3,4-α]isoindole;
methyl-{6-[3-(5-methyl-3-phenylisoxazol-4-yl)-5H-[1,2,4]triazolo[3,4-α]isoindol-8-yl]pyridin-2-yl}amine;
dimethyl-{6-[3-(5-methyl-3-phenylisoxazol-4-yl)-5H-[1,2,4]triazolo[3,4-α]isoindol-8-yl]pyridin-2-ylmethyl}amine;
methyl-{6-[3-(5-methyl-3-phenylisoxazol-4-yl)-5H-[1,2,4]triazolo[3,4-α]isoindol-8-yl]pyridin-2-ylmethyl}amine;
N,N'-trimethyl-N'-{6-[3-(5-methyl-3-phenylisoxazol-4-yl)-5H-[1,2,4]triazolo [3,4-α]isoindol-8-yl]pyridin-2-ylmethyl}ethane-1,2-diamine;
3-(5-methyl-3-phenylisoxazol-4-yl)-9-(pyridin-3-yl)-5H-[1,2,4]triazolo[3,4-α]isoindole;
3-(5-methyl-3-phenylisoxazol-4-yl)-8-(pyridin-4-yl)-5H-[1,2,4]triazolo [3,4-α]isoindole;
3-[3-(5-methyl-3-phenylisoxazol-4-yl-5H-[1,2,4]triazolo[3,4-α]isoindol-8-yl]-benzonitrile;
8-methyl-3-(5-methyl-3-phenylisoxazol-4-yl)-5H-[1,2,4]triazolo[3,4-α]isoindole;
3-(5-methyl-3-phenylisoxazol-4-yl)-5H-[1,2,4]triazolo[3,4-α]isoindole-8-carbonitrile;
8-bromo-3-(5-hydroxymethylenyl-3-[4-fluorophenyl]isoxazol-4-yl)-5H-[1,2,4]triazolo[3,4-a]isoindole;
8-bromo-3-(5-chloro-3-phenylisoxazol-4-yl)-5H-[1,2,4]triazolo[3,4-a]isoindole;
8-bromo-3-(5-[2-aminomethylpyridinyl)-3-phenylisoxazol-4-yl)-5H-[1,2,4]triazolo[3,4-a]isoindole;
3-(5-methyl-3-phenylisoxazol-4-yl)-5H-[1,2,4]triazolo[3,4-a]isoindol-8-ylamine;
3-(5-methyl-3-phenylisoxazol-4-yl)-8-(pyridin-3-ylmethoxy)-5H-[1,2,4]triazolo[3,4-α]isoindole;
3-(5-methyl-3-phenylisoxazol-4-yl)-8-(pyridin-2-ylmethoxy)-5H-[1,2,4]triazolo[3,4-α]isoindole;
3-(5-methyl-3-phenylisoxazol-4-yl)-8-(piperidin-4-yloxy)-5H-[1,2,4]triazolo[3,4-α]isoindole;
3-(5-methyl-3-phenylisoxazol-4-yl)-8-(1-methyl-1,2,3,6-tetrahydropyridin-4-yl)-5H-[1,2,4]triazolo[3,4-α]isoindole;
6-[3-(5-methyl-3-phenylisoxazol-4-yl)-5H-[1,2,4]triazolo [3,4-a]isoindol-8-yl]pyrazine-2-carboxylic acid
8-bromo-3-(5-fluoromethylenyl-3-[4-fluorophenyl]isoxazol-4-yl)-5H-[1,2,4]triazolo[3,4-a]isoindole; and
3-(5-methyl-3-phenylisoxazol-4-yl)-8-(pyridin-3-yl)-5H-[1,2,4]triazolo[3,4-α]isoindole;

and pharmaceutically acceptable salts thereof.

Where the compounds according to the invention have at least one asymmetric centre, they may accordingly exist as enantiomers. Where the compounds according to the invention possess one or more asymmetric centres, they may additionally exist as diastereoisomers. It is to be understood that all such isomers and mixtures thereof in any proportion are encompassed within the present invention.

For use in medicine, the compounds of formula (I) may be in the form of pharmaceutically acceptable salts. Hence in a favoured aspect this invention provides the compounds of formula (I) in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts and salts formed with suitable organic ligands, e.g. quaternary ammonium salts.

The compounds of the present invention have a good binding affinity (Ki) for the α5 subunit of the $GABA_A$ receptor. In a preferred embodiment the compounds of the present invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits. Particularly preferred are compounds which are both binding and functionally selective.

The invention also provides pharmaceutical compositions comprising one or more compounds of this invention and a pharmaceutically acceptable carrier. Preferably these compositions are in unit dosage form, such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or unsufflation. For preparing solid compositions such as tablets, the principal active ingredient is mixed with a pharmaceutical carrier, e.g. conventional tableting ingredients, such as corn starch, lactose, sucrose, sorbitol, talc, stearic acid, magnesium stearate, dicalcium phosphate or gums or surfactants, such as sorbitan monooleate, polyethylene glycol and other pharmaceutical diluents, e.g. water, to form a solid preformulation composition containing a homogeneous mixture of a compound of the present invention, or a pharmaceutically acceptable salt thereof. When referring to these preformulations as homogeneous, it is meant that the active ingredient is dispersed evenly throughout the composition so that the composition may be readily subdivided into equally effective unit dosage forms, such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment in the human body. Preferably the treatment is for a condition associated with $GABA_A$ receptors comprising the α5 subunit and/or for enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

The present invention further provides the use of a compound of the present invention in the manufacture of a medicament for the enhancement of cognition, preferably in a human being suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil as well as elixirs and similar pharmaceutical vehicles. Suitable dispersing or suspending agents for aqueous suspensions include synthetic and natural gums, such as tragacanth, acacia, alginate, dextran, sodium carboxymethylcellulose, methylcellulose, polyvinyl-pyrrolidone or gelatin.

For the enhancement of cognition, a suitable dosage level is about 0.01 to 250 mg/kg per day, preferably about 0.01 to 100 mg/kg per day and especially about 0.01 to 5 mg/kg of body weight per day. The compounds may be administered on a regimen of 1 to 4 times per day. In some cases, however, dosage outside these limits may be used.

The present invention also provides a process for the preparation of a compound of formula I, as defined above, which comprises reacting a compound of formula II:

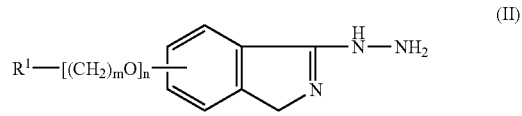

(II)

in which $R^1$, m and n are as defined above, with a compound of formula III:

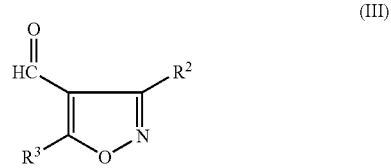

(III)

in which $R^2$ and $R^3$ are as defined above and are optionally protected. The reaction is typically carried out by formation of a hydrazone in the presence of an inert organic solvent, such as dichloromethane and in the presence of an acid such as 10% trifluoroacetic acid followed by oxidative cyclisation with bromine. If necessary deprotection of the product to achieve the compound of formula I is carried out.

The compound of formula II is produced by reacting a compound of formula IV with hydrazine:

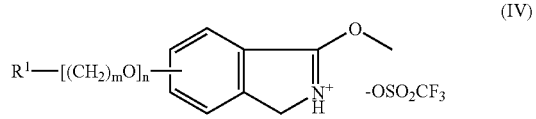
(IV)

wherein $R^1$, m and n are as defined above, generally in a solvent such as THF in the presence of a base such as triethylamine.

The compound of formula IV is prepared by reacting a compound of formula V with methyl trifluoromethanesulfonate:

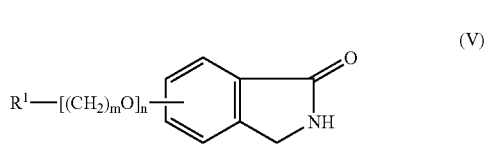
(V)

wherein $R^1$, m and n are as defined above, generally in a solvent such as dichloromethane for about an hour.

Where not commercially available, the compound of formula V can be prepared by reacting a compound of formula VI with ammonia:

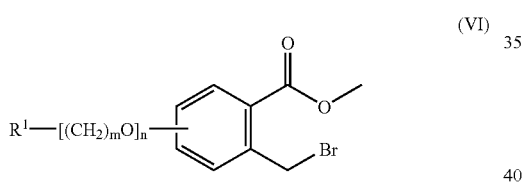
(VI)

wherein $R^1$, m and n are as defined above, generally in a mixture of solvents such as THF/methanol. The compounds of formula VI can be made by bromination of the appropriate derivative of methyl 2-methylbenzoate by reacting with a brominating agent such as N-bromo succinimide at reflux in carbon tetrachloride. The starting material is commercially available or can be made from commercially available compounds by known methods.

Alternatively, a compound of formula V may be prepared by reacting a compound of formula XIII with N-hydroxyphthalimide:

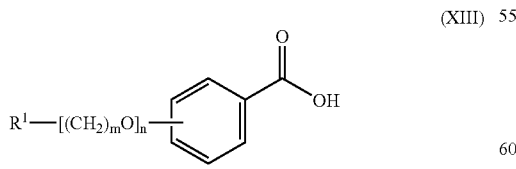
(XIII)

wherein $R^1$, m and n are defined above, generally in concentrated sulfuric acid for about 3 hours at about 80° C. Compounds of formula XIII are commercially available or may be made by known methods from commercially available compounds.

The compound of formula III can be prepared by reacting a compound of formula VII with a mild oxidizing agent such as Dess-Martin periodinane:

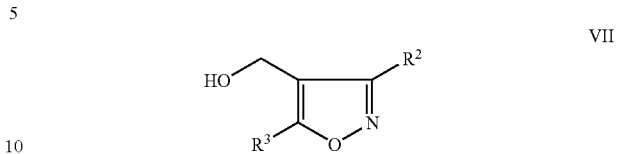
VII wherein $R^2$ and $R^3$ are as defined above, generally in a solvent such as dichloromethane in the presence of a base such as pyridine at room temperature for about 30 minutes.

The compound of formula VII can be produced by reducing a compound of formula VIII with a reagent such as diisobutyl aluminium hydride:

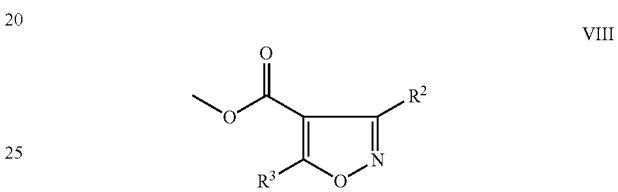
VIII wherein $R^2$ and $R^3$ are as defined above, generally in a solvent such as toluene at about −78° C. for about 1.5 hours.

The compound of formula VIII can be prepared by reacting a compound of formula IX with a compound of formula X:

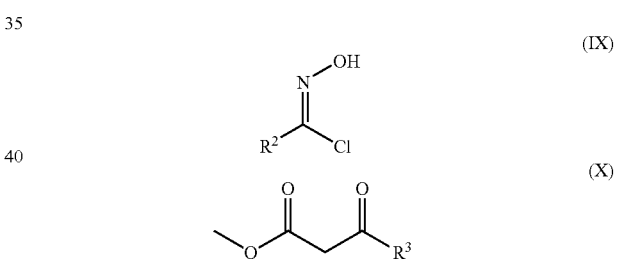
(IX)

(X)

wherein $R^2$ and $R^3$ are as defined above, generally in a water-free solvent such as anhydrous methanol in the presence of a strong base such as sodium methoxide for several hours. Where they are not commercially available, the compounds of formulae IX and X can be made from commercially available compounds by known methods.

In an alternative embodiment, compounds of formula I can be produced by cyclizing a compound of formula XI:

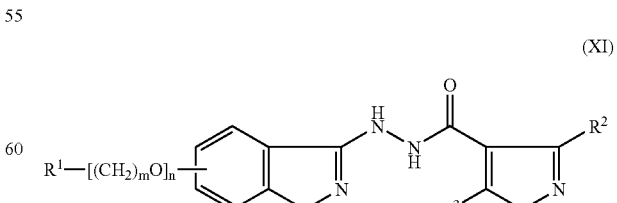
(XI)

wherein $R^1$, $R^2$, $R^3$, m and n are as defined above, generally in a solvent such as toluene in the presence of acid such as acetic acid at reflux for about 16 hours.

The compound of formula XI can be produced by reacting a compound of formula IV with a compound of formula XII:

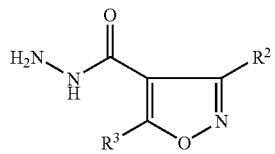
(XII)

wherein $R^2$ and $R^3$ are as defined above, generally in the presence of a base such as triethylamine and with heating at reflux for about 16 hours, optionally with the portionwise addition of the compound of formula XII and further heating at reflux for a further 16 hours. Compounds of formula XII are commercially available or can be prepared from commercially available compounds by known methods.

Compounds of formula I may also be produced by interconversion from other compounds of formula I as illustrated in the Examples.

It will also be appreciated that where more than one isomer can be obtained from a reaction then the resulting mixture of isomers can be separated by conventional means.

Where the above described process for the preparation of compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-d-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following non-limiting Examples serve to illustrate the present invention.

EXAMPLE 1

3-(5-Methyl-3-phenylisoxazol-4-yl)-5H-[1,2,4]triazolo[3,4-α]isoindole a) 3-Methoxy-1H-isoindolium trifluoromethanesulfonate 1H-Isoindolone (5 g, 38 mmol) in dichloromethane (100 ml) was stirred with methyl trifluoromethanesulfonate (6.38 ml, 56 mmol) for one hour. The solvent was removed and the residue was triturated with ether and dried to yield product. (9.5 g, 86%). $^1$H NMR (360 MHz, d6 DMSO) δ 7.97 (1H, d, J=7.2 Hz), 7.90–7.83 (2H,m), 7.67 (1H, t, J=7.2 Hz), 5.04 (2H, s), 4.38 (3H, s), m/z (ES$^+$) 148 (M$^+$).

b) 5-Methyl-3-phenylisoxazole-4-carboxylic acid N'-(3H-isoindol-1-yl)hydrazide

To a solution of 3-methoxy-1H-isoindolium trifluoromethanesulfonate (1 g, 3.4 mmol) in ethanol (40 ml) was added 5-methyl-3-phenyl-4-isoxazoyl hydrazide (0.878 g, 4.04 mmol) and triethylamine (0.7 ml, 5.05 mmol). After heating to reflux for sixteen hours another portion of 5-methyl-3-phenyl-4-isoxazoyl hydrazide (0.878 g, 4.04 mmol) was added and the reaction was heated to reflux for a further sixteen hours. The reaction was cooled and the resulting precipitate was filtered to give product as a yellow solid. (0.875 g, 78%). $^1$H NMR (360 MHz, d6 DMSO) δ 10.18 (1H, s), 7.75–7.28 (10H, in), 4.55 (2H, s), 2.56 (3H, s), m/z (ES$^+$) 333 (M+H)$^+$.

c) 3-(5-Methyl-3-phenylisoxazol-4-yl)-5H-[1,2,4]triazolo[3,4-a]isoindole

5-Methyl-3-phenylisoxazole-4-carboxylic acid N'-(3H-isoindol-1-yl)hydrazide (0.1 g, 0.31 mmol) was suspended in toluene (20 ml) and acetic acid (0.4 ml) was added. The reaction was heated to reflux for 16 hours and the solvent was removed and the residue was dissolved in dichloromethane and washed with water. The organic layer was dried, filtered and evaporated to yield a residue which was purified by column chromatography on silica using isohexane and ethyl acetate (1:1) to yield the title compound (26 mg, 27%), $^1$H NMR (500 MHz, CDCl$_3$) δ 8.01 (1H, d, J=7.5 Hz), 7.55–7.39 (7H, m), 7.27 (1H, d, J=7.5 Hz), 4.02 (2H, s), 2.70 (3H,s), m/z (ES$^+$) 315 (M+H)$^+$.

EXAMPLE 2

8-Methoxy-3-(5-methyl-3-phenylisoxazol-4-yl)-5H-[1,2,4]triazolo[3,4-a]isoindole a) 3,5-Dimethoxy-1H-isoindolium trifluoromethanesulfonate Prepared in a similar manner to that of Example 1a using 6-methoxy-2,3-dihydro isoindol-1-one (Daiichi Yakka Daigaku Kenkyu Nenpo 1989, 20, 1–10.)

$^1$H NMR (400 MHz, d6 DMSO) δ 7.73 (1H, d, J=8 Hz), 7.45 (1H, d, J=8 Hz), 7.45 (1H, s), 4.98 (2H, s), 3.95 (3H, s) m/z (ES$^+$) 178 (M)$^+$.

b) 8-Methoxy-3-(5-methyl-3-phenylisoxazol-4-yl)-5H-[1,2,4]triazolo[3,4-a]isoindole 3,5-Dimethoxy-1H-isoindolium trifluoromethanesulfonate (3.2 g, 9.8 mmol) in ethanol (50 ml) with triethylamine (0.99 g, 9.8 mmol) was stirred with hydrazine hydrate for one hour, the reaction mixture was evaporated and azeotroped with dry toluene. The residue was dissolved in 10% trifluoroacetic acid in dichloromethane and 5-methyl-3-phenyl-4-isoxazole carboxaldehyde was added (1.87 g, 10 mmol) and the reaction was stirred for 0.5 hours. The solvent was removed and the residue was partitioned between ethyl acetate and water and the organic layer was washed with saturated sodium hydrogen carbonate, dried, filtered and evaporated. The residue was taken up into methanol (50 ml), sodium acetate was added and the stirred suspension was treated dropwise with bromine (0.5 ml). The reaction was diluted with water and extracted into dichloromethane and dried, filtered and evaporated. The product was purified by silica chromatography using ethyl acetate as eluant to yield the title compound (1.1 g, 32%). $^1$H NMR (360 MHz, d6 DMSO) δ 7.52–7.41 (7H, m), 7.04 (1H, dd, J=2.4, 8.4 Hz), 4.44 (2H, s), 3.85 (3H, s), 2.60 (3H, s), m/z (ES$^+$) 345 (M+H)$^+$.

EXAMPLE 3

3-(5-Methyl-3-phenylisoxazol-4-yl)-8-(1-methyl-1H-[1,2,4]triazol-3-ylmethoxy)-5H-[1,2,4]triazolo[3,4-a]isoindole a) 3-(5-Methyl-3-phenylisoxazol-4-yl)-5H-[1,2,4]triazolo[3,4-a]isoindol-8-ol 8-Methoxy-3-(5-methyl-3-phenylisoxazol-4-yl)-5H-[1,2,4]triazolo[3,4-a]isoindole (4.6 g, 13 mmol) in dichloromethane (70 ml) was stirred with boron tribromide (25 g) for five days. The reaction was cooled to −78° C. and diethyl ether was added dropwise followed by water. The reaction was warmed to room temperature and the organic layer was washed with water and dried, filtered and evaporated. The residue was purified by column chromatography on silica using methanol/dichloromethane to yield the title compound.

$^1$H NMR (360 MHz, d6 DMSO) δ 10.10 (1H, brs), 7.52–7.44 (5H, m), 7.33 (1H, d, J=7.2 Hz), 7.25 (1H, d, J=2 Hz), 6.90 (1H, dd, J=7.2, J=2 Hz), 4.43 (2H, s), 2.6 (3H, s), m/z (ES$^+$) 331 (M+H)$^+$.

b) 3-(5-Methyl-3-phenylisoxazol-4-yl)-8-(1-methyl[1,2,4]triazol-3-ylmethoxy)-5H-[1,2,4]triazolo[3,4-a]isoindole 3-(5-Methyl-3-phenylisoxazol-4-yl)-5H-[1,2,4]triazolo[3,4-a]isoindol-8-ol (35 mg) and potassium carbonate (30 mg) and 5-(chloromethyl)-2-methyltriazole were heated together with DMF (1 ml) at 120° C. for 2 hours. The reaction was diluted with water and extracted with ethyl acetate. The organic layer was washed with water (×5), dried and evaporated to yield an oil which was purified by column chromatography on silica using methanol/dichloromethane to yield the title compound (7.8 mg).

$^1$H NMR (360 MHz, d6 DMSO) δ 8.05 (1H, s), 7.67 (1H, d, J=2 Hz, 7.53–7.38 (5H, m), 7.18–7.07 (2H, m), 5.21 (2H, s), 3.96 (2H, s), 3.94 (3H, s), 2.70 (3H, s). m/z (ES$^+$) 426 (M+H)$^+$.

EXAMPLE 4

8-Bromo-3-(5-methyl-3-phenylisoxazol-4-yl)-5H-[1,2,4]triazolo[3,4-a]isoindole a) 6-Bromo-2,3-dihydroisoindol-1-one Methyl 2-bromomethyl-5-bromobenzoate (0.1 mol) was dissolved in THF/methanol (200 ml) (1:1) and the solution obtained was saturated with dry ammonia gas. The solvent was removed and the residue was triturated with water, diethyl ether and hexane and then recrystallised from ethanol/dichloromethane to obtain 6-bromo-2,3-dihydro-isoindol-1-one (12.5 g). $^1$H NMR (400 MHz, d6 DMSO) δ 8.70 (1H, bs), 7.78 (1H,s), 7.77 (1H, d, J=7 Hz), 7.55 (1H, d, J=7 Hz), 4.35 (2H,s). m/z (ES$^+$) 212 (M$^+$).

b) 5-Bromo-3-methoxy-1H-isoindolium trifluoromethanesulfonate

Prepared in a similar manner to that of Example 1a using 6-bromo-2,3-dihydro-isoindol-1-one. $^1$H NMR (360 MHz, CDCl$_3$) δ 12.5 (1H, brs), 8.05 (1H,d, J=1 Hz), 7.94 (1H, dd, J=7 and 1 Hz), 7.66 (1H, dd, J=7 and 1 Hz), 5.07 (2H, s), 4.60 (3H, s). m/z (ES$^+$) 226 (M$^+$).

c) (6-Bromo-3H-isoindol-1-yl)hydrazine

5-Bromo-3-methoxy-1H-isoindolium trifluoromethanesulfonate (3.7 g) was dissolved in THF (35 ml) and triethylamine (2.8 ml) was added followed by hydrazine (1 M in THF, 35 ml). After an hour the solid which had precipitated was filter off and dried to give title compound (2.8 g) $^1$H NMR (360 MHz, CDCl$_3$) δ 12.5 (1H, brs), 7.85 (1H,d, J=1 Hz), 7.51 (1H, dd, J=7 and 1 Hz), 7.25 (1H, dd, J=7 and 1 Hz), 4.49 (2H, s). m/z (ES$^+$) 226 (M$^+$).

d) 8-Bromo-3-(5-methyl-3-phenylisoxazol-4-yl)-5H-[1,2,4]triazolo[3,4-a]isoindole (6-Bromo-3H-isoindol-1-yl)hydrazine (2.8 g) was stirred in 10% trifluoroacetic acid in dichloromethane (40 ml) and 5-methyl-3-phenyl-4-isoxazole carboxaldehyde was added (2.33 g) and the reaction was stirred for 0.5 hours. The solvent was removed and the residue was partitioned between ethyl acetate and water and the organic layer was washed with saturated sodium hydrogen carbonate, dried, filtered and evaporated. The residue was taken up into methanol and dichloromethane, sodium acetate was added and the stirred suspension was treated dropwise with bromine (0.5 ml). The reaction was diluted with water and extracted into dichloromethane and dried, filtered and evaporated. The product was purified by silica chromatography using ethyl acetate as eluant to yield the title compound (1.46 g).

$^1$H NMR (400 MHz, d6 DMSO) δ 8.13 (1H,d, J=1 Hz), 7.68 (1H, dd, J=7 and 1 Hz), 7.53–7.43 (6H, m), 4.54 (2H, s), 2.60 (3H, s). m/z (ES$^+$) 394 (M$^+$).

EXAMPLE 5

6-Bromo-3-(5-methyl-3-phenylisoxazol-4-yl)-5H-[1,2,4]triazolo[3,4-a]isoindole

Prepared in a similar manner to Example 4 using 4-bromo-2,3-dihydro-isoindol-1-one, $^1$H NMR (400 MHz, d6 DMSO) δ 7.97 (1H,d, J=7 Hz), 7.72(1H, d, J=7), 7.55–7.45 (6H,m), 4.47 (2H, s), 2.63 (3H, s). m/z (ES$^+$) 394 (M$^+$).

EXAMPLE 6

8-(4,5-Dihydro-1H-imidazol-2-yl)-3-(5-methyl-3-phenylisoxazol-4-yl)-5H-[1,2,4]triazolo[3,4-a]isoindole a) 6-Iodo-2,3-dihydroisoindol-1-one 3-Iodobenzoic acid (50 g, 0.2 mol) and N-hydroxymethylphthalimide (35.7 g, 0.2 mol) were suspended in concentrated sulfuric acid (200 ml) and heated for three hours at 80° C. The reaction mixture was poured onto ice and the product was filtered, washed with water and dilute ammonium hydroxide and then stirred in hot (70° C.) ethanol for 1.5 hours before cooling and drying to yield the title compound (24 g, 45%). $^1$H NMR (360 MHz, d6 DMSO) δ 8.63 (1H, brs), 7.95 (1H, s), 7.92 (1H, d, J=7 and 1 Hz), 7.42 (1H, d, J=7 and 1 Hz), 4.33 (2H, s). m/z (ES$^+$) 260 (M$^+$).

b) 5-Iodo-3-methoxy-1H-isoindolium trifluoromethanesulfonate

Prepared in a similar manner to that of Example 1a using 6-iodo-2,3-dihydro-isoindol-1-one. $^1$H NMR (360 MHz, CDCl$_3$) δ 12.5 (1H, brs), 8.26 (1H,d, J=1 Hz), 8.14 (1H, dd, J=7 and 1 Hz), 7.53 (1H, d, J=7 Hz), 5.06 (2H, s), 4.58 (3H, s). m/z (ES$^+$) 274 (M$^+$).

c) 5-Methyl-3-phenylisoxazole-4-carboxylic acid NA-(6-iodo-3H-isoindol-1-yl)-hydrazide Prepared in a similar manner to that of Example 1b using 5-Iodo-3-methoxy-1H-isoindolium trifluoromethanesulfonate d) 8-Iodo-3-(5-methyl-3-phenylisoxazol-4-yl)-5H-[1,2,4]triazolo[3,4-a]isoindole 5-Methyl-3-phenylisoxazole-4-carboxylic acid N'-(6-iodo-3H-isoindol-1-yl)-hydrazide (19.96 g) was heated in acetic acid (200 ml) at reflux for five hours. The reaction was cooled and evaporated. The residue was purified by column chromatography on silica using 40% ethyl acetate/isohexane to yield 8-iodo-3-(5-methyl-3-phenylisoxazol-4-yl)-5H-[1,2,4]-triazolo[3,4-a]isoindole (5.6 g). $^1$H NMR (360 MHz, CDCl$_3$) 7.72 (1H,d, J=1 Hz), 7.53–7.34 (6H,m), 7.01 (1H, d, J=7 Hz) 3.93 (2H, s), 2.71 (3H, s). m/z (ES$^+$) 441 (M$^+$).

e) 3-(5-Methyl-3-phenylisoxazol-4-yl)-5H-[1,2,4]triazolo[3,4-a]isoindole-8-carboxylic acid methyl ester 8-Iodo-3-(5-methyl-3-phenylisoxazol-4-yl)-5H-[1,2,4]triazolo[3,4-a]isoindole (3.1 g), triethylamine (6 ml) and tetrakis(triphenylphosphine)palladium(0) (0.5 g) were suspended in a degassed mixture of 1,4-dioxane (50 ml) and methanol (100 ml). The reaction was heated to 75° C. and a slow stream of carbon monoxide was passed through the reaction mixture for 16 hours. The reaction was evaporated and purified by column chromatography on silica to yield the title compound (1.9 g). $^1$H NMR (360 MHz, CDCl$_3$) 8.46 (1H, s), 7.83 (1H, d, J=7 Hz), 7.45–7.37 (5H, m), 7.24 (1H, d, J=7 Hz), 4.01(2H, s), 3.79 (3H, s), 2.71(3H, s). m/z (ES$^+$) 373 (M$^+$).

f) 8 (2-Imidazolinyl)-3-(5-methyl-3-phenylisoxazol-4-yl)-5H-[1,2,4]triazolo[3,4-a]isoindole Ethylenediamine (160 mg) in toluene (5 ml) was cooled to 5° C. and trimethylaluminium (2 M in toluene, 1 ml) was added. The reaction mixture was allowed to warm to 25° C. and then 3-(5-methyl-3-phenylisoxazol-4-yl)-5H-[1,2,4]triazolo[3,4-a]isoindole-8-carboxylic acid methyl ester (200 mg) was added and the reaction mixture was heated to reflux for 2 hours. The reaction was cooled, methanol was added and the reaction was evaporated and the residue was purified by column chromatography on silica to yield the title compound after recrystallisation from ethyl acetate (80 mg). $^1$H NMR (360 MHz, d6 DMSO) δ 8.32 (1H, s), 7.96 (1H, dd, J=7 and 1 Hz), 7.56–7.41 (6H, m), 4.59 (2H, s), 3.66 (3H, s), 2.59 (3H, s). m/z (ES$^+$) 383(M$^+$).

EXAMPLE 7

3-(5-Methyl-3-phenylisoxazol-4-yl)-8-pyridin-2-yl-5H-[1,2,4]triazolo[3,4-α]isoindole A mixture of 8-bromo-3-(5-methyl-3-phenylisoxazol-4-yl)-5H-[1,2,4]triazolo[3,4-a]isoindole (290 mg) prepared as in Example 4), bis(pinacolato)diboron (226 mg), KOAc (218 mg) and dioxane (10 ml) was degassed with a stream of N$_2$ for 0.5 h. Bis(triphenylphosphine)palladium(II) chloride (5 mg) was added and the reaction heated to 80° C. for 4 h. The reaction was cooled, 2-bromopyridine (0.14 ml), Cs$_2$CO$_3$ (1.2 g/2 ml H$_2$O), and bis(triphenylphosphine)palladium(II) chloride (14 mg) were added and heated at 80° C. for 3 days. The reaction mixture was cooled, poured into H$_2$O and extracted into CH$_2$Cl$_2$, dried (MgSO$_4$), and concentrated under reduced pressure. The residue was purified by column chromatography on silica, eluting with 1.5% MeOH/CH$_2$Cl$_2$, and recrystallised from CH$_2$Cl$_2$/hexane to give the title compound (20 mg, 7%). $^1$H NMR (500 MHz, CDCl$_3$) δ 8.73 (1H, d, J=4.5 Hz), 8.58 (1H, s), 8.16 (1H, d, J=7.5 Hz), 7.84–7.79 (2H, m), 7.56–7.55 (2H, m), 7.49–7.29 (5H, m), 4.07 (2H, s), 2.73 (3H, s), m/z (ES$^+$) 392 (M+H)$^+$.

EXAMPLE 8

3-(5-Methyl-3-phenylisoxazol-4-yl)-8-pyrimidin-5-yl-5H-[1,2,4]triazolo[3,4-α]isoindole Prepared in a similar manner to Example 7 using 5-bromopyrimidine to give the title compound (60 mg, 40%). $^1$H NMR (400 MHz, CDCl$_3$) δ 9.27 (1H, s), 9.00 (2H, s), 8.24 (1H, s), 7.63–7.40 (7H, m), 4.08 (2H, s), 2.73 (3H, s), m/z (ES$^+$) 393 (M+H)$^+$.

EXAMPLE 9

3-(5-Methyl-3-phenylisoxazol-4-yl)-8-(6-methylpyridazin-3-yl)-5H-[1,2,4]triazolo[3,4-α]isoindole Prepared in a similar manner to Example 7 using 3-chloro-6-methylpyridazine to give the title compound (75 mg, 61%). $^1$H NMR (400 MHz, CDCl$_3$) δ 8.54 (1H, d, J=1.2 Hz), 8.33 (1H, dd, J=9.7, 1.6 Hz), 7.83 (1H, d, J=8.7 Hz), 7.57–7.40 (7H, m), 4.08 (2H, s), 2.80 (3H, s), 2.73 (3H, s), m/z (ES$^+$) 407 (M+H)$^+$.

EXAMPLE 10

3-(5-Methyl-3-phenylisoxazol-4-yl)-8-pyrimidin-2-yl-5H-[1,2,4]triazolo[3,4-α]isoindole Prepared in a similar manner to Example 7 using 2-bromopyrimidine to give the title compound (14 mg, 12%). $^1$H NMR (500 MHz, CDCl$_3$) δ 9.15 (1H, s), 8.85 (2H, s), 8.53 (1H, dd, J=8, 1.5 Hz), 7.56 (2H, dd, J=2.5, 1 Hz), 7.49–7.37 (4H, m), 7.27–7.25 (1H, m), 4.08 (2H, s), 2.73 (3H, s), m/z (ES$^+$) 393 (M+H)$^+$.

EXAMPLE 11

3-(5-Methyl-3-phenylisoxazol-4-yl)-8-thiazol-2-yl-5H-[1,2,4]triazolo[3,4-α]isoindole Prepared in a similar manner to Example 7 using 2-bromothiazole to give the title compound (8 mg, 7%). $^1$H NMR (400 MHz, CDCl$_3$) δ 8.56 (1H, d, J=1.2 Hz), 8.09 (1H, dd, J=8.1, 1.6 Hz), 7.91 (1H, d, J=3.2 Hz), 7.56–7.54 (2H, m), 7.48–7.34 (5H, m), 4.05 (2H, s), 2.72 (3H, s), m/z (ES$^+$) 398 (M+H)$^+$.

EXAMPLE 12

3-Methyl-5-[3-(5-methyl-3-phenylisoxazol-4-yl)-5H-[1,2,4]triazolo[3,4-α]isoindol-8-yl]-pyridin-2-ylamine Prepared in a similar manner to Example 7 using 2-amino-5-bromo-3-methylpyridine to give the title compound (30 mg, 24%). $^1$H NMR (360 MHz, CDCl$_3$) δ 8.22 (1H, d, J=2.2 Hz), 8.15 (1H, d, J=1.3 Hz), 7.56–7.53 (4H, m), 7.49–7.39 (3H, m), 7.30 (1H, d, J=8.1 Hz), 4.04 (2H, s), 2.72 (3H, s), 2.23 (3H, s), m/z (ES$^+$) 421 (M+H)$^+$.

EXAMPLE 13

5-[3-(5-Methyl-3-phenylisoxazol-4-yl)-5H-[1,2,4]triazolo[3,4-α]isoindol-8-yl]-nicotinamide Prepared in a similar manner to Example 7 using 3-bromonicotinamide to give the title compound (34 mg, 26%). $^1$H NMR (360 MHz, CDCl$_3$) δ 9.05 (2H, d, J=2.0 Hz), 8.44 (1H, t, J=2.2), 8.29 (1H, s), 7.68 (1H, dd, J=8.1, 1.7 Hz), 7.55 (2H, dd, J=6.6, 4.3 Hz), 7.51–7.41 (4H, m), 4.08 (2H, s), 2.73 (3H, s), m/z (ES$^+$) 435 (M+H)$^+$.

EXAMPLE 14

8-Isothiazol-5-yl-3-(5-methyl-3-phenylisoxazol-4-yl)-5H-[1,2,4]triazolo[3,4-α]isoindole Prepared in a similar manner to Example 7 using 5-bromoisothiazole to give the title compound (55 mg, 46%). $^1$H NMR (400 MHz, CDCl$_3$) δ 8.52 (1H, d, J=1.8 Hz), 8.27 (1H, d, J=1.4), 7.64 (1H, dd, J=7.9, 1.6 Hz), 7.56–7.53 (2H, m), 7.50–7.35 (5H, m), 4.05 (2H, s), 2.73 (3H, s), m/z (ES$^+$) 398 (M+H)$^+$.

EXAMPLE 15

3-(5-Methyl-3-phenylisoxazol-4-yl)-8-thiazol-4-yl-5H-[1,2,4]triazolo[3,4-α]isoindole Prepared in a similar manner to Example 7 using 4-bromothiazole (Synthesis, 1986, 9, 757–60) to give the title compound (50 mg, 42%). $^1$H NMR (400 MHz, CDCl$_3$) δ 8.92 (1H, s), 8.52 (1H, d, J=1.1 Hz), 8.08 (1H, dd, J=8.0, 1.6 Hz), 7.67 (1H, d, J=1.9 Hz), 7.57–7.54 (2H, m), 7.47–7.40 (3H, m), 7.35 (1H, dd, J=8.2, 0.6 Hz), 4.05 (2H, s), 2.72 (3H, s), m/z (ES$^+$) 398 (M+H)$^+$.

EXAMPLE 16

3-(5-Methyl-3-phenylisoxazol-4-yl)-8-pyrazin-2-yl-5H-[1,2,4]triazolo[3,4-α]isoindole Prepared in a similar manner to Example 7 using chloropyrazine to give the title compound (25 mg, 25%). $^1$H NMR (360 MHz, CDCl$_3$) δ 9.10 (1H, d, J=1.5 Hz), 8.68–8.67 (2H, m), 8.58 (1H, d, J=2.4 Hz), 8.12 (1H, dd, J=8.1, 1.6 Hz), 7.57–7.54 (2H, m), 7.48–7.40 (4H, m), 4.08 (2H, s), 2.73 (3H, s), m/z (ES$^+$) 393 (M+H)$^+$.

EXAMPLE 17

8-(2,6-Dimethoxypyrimidin-4-yl)-3-(5-methyl-3-phenylisoxazol-4-yl)-5H-[1,2,4]triazolo[3,4-α]isoindole Prepared in a similar manner to Example 7 using 6-chloro-2,4-dimethoxypyrimidine to give the title compound (19 mg, 14%). $^1$H NMR (400 MHz, CDCl$_3$) δ 8.68 (1H, d, J=1.2 Hz), 8.12 (1H, dd, J=8.1, 1.7 Hz), 7.56–7.36 (6H, m), 6.84 (1H, s), 4.11 (3H, s), 4.06 (2H, s), 4.04 (3H, s), 2.73 (3H, s), m/z (ES$^+$) 453 (M+H)$^+$.

EXAMPLE 18

8-(6-Methoxypyridazin-3-yl)-3-(5-methyl-3-phenylisoxazol-4-yl)-5H-[1,2,4]triazolo[3,4-α]isoindole Prepared in a similar manner to Example 7 using 3-chloro-6-methoxypyridazine to give the title compound (9 mg, 8%). $^1$H NMR (360 MHz, CDCl$_3$) δ 8.50 (1H, s), 8.26 (1H, dd, J=8.1, 1.5 Hz), 7.85 (1H, d, J=9.2 Hz), 7.56–7.40 (6H, m), 7.12 (1H, d, J=9.3 Hz), 4.21 (3H, s), 4.08 (2H, s), 2.73 (3H, s), m/z (ES$^+$) 423 (M+H)$^+$.

EXAMPLE 19

8-Furan-3-yl-3-(5-methyl-3-phenylisoxazol-4-yl)-5H-[1,2,4]triazolo[3,4-α]isoindole Prepared in a similar manner to Example 7 using 3-bromofuran to give the title compound (11 mg, 10%). $^1$H NMR (400 MHz, CDCl$_3$) δ 8.13 (1H, d, J=1.2 Hz), 7.81 (1H, s), 7.56–7.39 (6H, in), 7.28–7.26 (2H, in), 6.75–6.74 (1H, m), 4.03 (2H, s), 2.72 (3H, s), m/z (ES$^+$) 381 (M+H)$^+$.

EXAMPLE 20

6-[3-(5-Methyl-3-phenylisoxazol-4-yl)-5H-[1,2,4]triazolo[3,4-α]isoindol-8-yl]-pyridazin-3-ylamine Prepared in a similar manner to Example 7 using 3-amino-6-chloropyridazine to give the title compound (34 mg, 28%). $^1$H NMR (400 MHz, CDCl$_3$) δ 8.42 (1H, d, J=1.0 Hz), 8.17–8.20 (1H, m), 7.77 (1H, d, J=9.2 Hz), 7.54–7.39 (6H, m), 6.94 (1H, d, J=9.2 Hz), 4.09 (2H, s), 2.72 (3H, s), m/z (ES$^+$) 408 (M+H)$^+$.

EXAMPLE 21

3-(5-Methyl-3-phenylisoxazol-4-yl)-8-(2-methylpyridin-4-yl)-5H-[1,2,4]triazolo[3,4-α]isoindole Prepared in a similar manner to Example 7 using 4-bromo-2-methylpyridine (Rocz. Chem., 1968, 42(12), 2061–76) to give the title compound (18 mg, 15%). $^1$H NMR (360 MHz, CDCl$_3$) δ 8.60 (1H, d, J=5.2 Hz), 8.28 (1H, s), 7.66 (1H, d, J=6.9 Hz), 7.55 (2H, d, J=6.9 Hz), 7.48–7.34 (6H, m), 4.07 (2H, s), 2.73 (3H, s), 2.66 (3H, s), m/z (ES$^+$) 406 (M+H)$^+$.

EXAMPLE 22

3-(5-Methyl-3-phenylisoxazol-4-yl)-8-(2-methylpyridin-3-yl)-5H-[1,2,4]triazolo[3,4-α]isoindole Prepared in a similar manner to Example 7 using 3-bromo-2-methylpyridine (Bull. Soc. Chim. Fr., 1972, 6, 2466–81) to give the title compound (23 mg, 19%). $^1$H NMR (400 MHz, CDCl$_3$) δ 8.56 (1H, dd, J=4.8, 1.7 Hz), 7.98 (1H, s), 7.58–7.41 (6H, m), 7.36 (2H, d, J=1.3 Hz), 7.26–7.22 (1H, m), 4.08 (2H, s), 2.72 (3H, s), 2.52 (3H, s), m/z (ES$^+$) 406 (M+H)$^+$.

EXAMPLE 23

3-(5-Methyl-3-phenylisoxazol-4-yl)-8-(6-methylpyrazin-2-yl)-5H-[1,2,4]triazolo[3,4-α]isoindole Prepared in a similar manner to Example 7 using 2-chloro-6-methylpyrazine (Tetrahedron, 1972, 28(15), 4155–70) to give the title compound. $^1$H NMR (400 MHz, CDCl$_3$) δ 9.90 (1H, s), 8.70 (1H, s), 8.46 (1H, s), 8.11 (1H, dd, J=8.0, 1.4 Hz), 7.56–7.39 (6H, m), 4.08 (2H, s), 2.73 (3H, s), 2.66(3H, s), m/z (ES$^+$) 407 (M+H)$^+$.

EXAMPLE 24

Methyl-{6-[3-(5-methyl-3-phenylisoxazol-4-yl)-5H-[1,2,4]triazolo[3,4-α]isoindol-8-yl]-pyridazin-3-yl}-amine a) 8-(6-Chloropyridazin-3-yl)-3-(5-methyl-3-phenylisoxazol-4-yl)-5H-[1,2,4]triazolo[3,4-α]isoindole Prepared in a similar manner to Example 7 using 3-chloro-6-iodopyridazine (Tetrahedron, 1999, 55(52), 15067–15070) to give the title compound (190 mg, 25%).

$^1$H NMR (400 MHz, CDCl$_3$) δ 8.55 (1H, d, J=1.4 Hz), 8.31 (1H, dd, J=8.1, 1.6 Hz), 7.91 (1H, d, J=8.3 Hz), 7.65 (1H, d, J=9.0 Hz), 7.57–7.54 (2H, m), 7.48–7.40 (4H, m), 4.09 (2H, s), 2.73 (3H, s), m/z (ES$^+$) 427 (M+H)$^+$.

b) Methyl-{6-[3-(5-methyl-3-phenylisoxazol-4-yl)-5H-[1,2,4]triazolo[3,4-α]isoindol-8-yl]pyridazin-3-yl}amine 8-(6-Chloropyridazin-3-yl)-3-(5-methyl-3-phenylisoxazol-4-yl)-5H-[1,2,4]triazolo[3,4-α]isoindole was heated in a sealed tube with methylamine (3 ml of 40% solution in water) for 16 h. The reaction mixture was cooled, poured into H$_2$O and extracted into CH$_2$Cl$_2$, dried (MgSO$_4$), and concentrated under reduced pressure.

Purified on alumina prep plates eluting with 3% MeOH/CH$_2$Cl$_2$ to give the title compound (12 mg, 24%). $^1$H NMR (360 MHz, CDCl$_3$) δ 8.42 (1H, d, J=1.2 Hz), 8.25 (1H, dd, J=8.1, 1.6 Hz), 7.72 (1H, d, J=9.4 Hz), 7.56–7.37 (6H, m), 6.82 (1H, d, J=9.4 Hz), 4.06 (2H, s), 3.10 (3H, s), 2.72 (3H, s), m/z (ES$^+$) 422 (M+H)$^+$.

EXAMPLE 25

N,N,N'-Trimethyl-N'-{6-[3-(5-methyl-3-phenylisoxazol-4-yl)-5H-[1,2,4]triazolo[3,4-α]isoindol-8-yl]pyridazin-3-yl}ethane-1,2-diamine Prepared in a similar manner to Example 24 using N,N,N'-trimethylethylene diamine to give the title compound (49 mg, 43%). $^1$H NMR (400 MHz, CDCl$_3$) δ 8.43 (1H, d, J=1.3 Hz), 8.29 (1H, dd, J=8.2, 1.6 Hz), 7.69 (1H, d, J=9.5 Hz), 7.56–7.54 (2H, m), 7.47–7.35 (4H, m), 6.91 (1H, d, J=9.6 Hz), 4.05 (2H, s), 3.48 (2H, t, J=7.0 Hz), 3.22 (3H, s), 2.72 (3H, s), 2.62 (2H, t, J=7.1 Hz), 2.34 (6H, s), m/z (ES$^+$) 493 (M+H)$^+$.

EXAMPLE 26

3-(5-Methyl-3-phenylisoxazol-4-yl)-8-(6-methylpyridin-2-yl)-5H-[1,2,4]triazolo[3,4-α]isoindole a) 8-(5,5-Dimethyl-[1,3,2]dioxaborinan-2-yl)-3-(5-methyl-3-phenylisoxazol-4-yl)-5H-[1,2,4]triazolo[3,4-α]isoindole A mixture of 8-bromo-3-(5-methyl-3-phenylisoxazol-4-yl)-5H-[1,2,4]triazolo[3,4-a]isoindole (290 mg) (prepared as in Example 4), bis(neopentyl glycolato)diboron (201 mg), KOAc (218 mg) and dioxane (5 ml) was degassed with a stream of N$_2$ for 0.5 h. Bis(triphenylphosphine)palladium(II) chloride (5 mg) was added and the reaction heated to 90° C. for 2 h. The reaction mixture was cooled, poured into H$_2$O and extracted into EtOAc, dried (MgSO$_4$), and concentrated under reduced pressure and was used without further purification in the next step.

b) 3-(5-Methyl-3-phenylisoxazol-4-yl)-8-(6-methyl-pyridin-2-yl)-5H-[1,2,4]triazolo[3,4-α]isoindole A mixture of 8-(5,5-dimethyl-[1,3,2]dioxaborinan-2-yl)-3-(5-methyl-3-phenylisoxazol-4-yl)-5H-[1,2,4]triazolo[3,4-α]isoindole (315 mg), 2-bromo-6-methylpyridine (0.34 ml), Cs$_2$CO$_3$ (1 g/1 ml H$_2$O), and dioxane (10 ml) was degassed with a stream of N$_2$ for 0.5 h. Bis(triphenylphosphine)palladium(II) chloride (15 mg) was added and heated at reflux for 2 h. The reaction mixture was cooled, poured into H$_2$O and extracted into CH$_2$Cl$_2$, dried (MgSO$_4$), and concentrated under reduced pressure. The residue was purified by column chromatography on silica, eluting with 1.5% MeOH/CH$_2$Cl$_2$, and recrystallised from CH$_2$Cl$_2$/hexane to give the title compound (78 mg, 26%). $^1$H NMR (360 MHz, CDCl$_3$) δ 8.60 (1H, d, J=1.2 Hz), 8.12 (1H, dd, J=8.1, 1.5 Hz), 7.69 (1H, t, J=7.7 Hz), 7.59–7.54 (3H, m), 7.47–7.34 (4H, m), 7.16 (1H, d, J=7.6 Hz), 4.06 (2H, s), 2.73 (3H, s), 2.64 (3H, s), m/z (ES$^+$) 406 (M+H)$^+$.

EXAMPLE 27

3-(5-Methyl-3-phenylisoxazol-4-yl)-8-(4-methyl-3,4,5,6-tetrahydro-2H-[1,2']bipyrazinyl-6-yl)-5H-[1,2,4]triazolo[3,4-α]isoindole Prepared in a similar manner to Example 26 using 2-chloro-6-(4'-methylpiperazin-1-yl) pyrazine hydrochloride (DE 2617205) to give the title compound (40 mg, 35%). $^1$H NMR (400 MHz, CDCl$_3$) δ 8.69 (1H, s), 8.37 (1H, s), 8.14 (1H, s), 8.01 (1H, dd, J=8.2, 1.6 Hz), 7.56–7.54 (2H, m), 7.49–7.39 (3H, m), 7.35 (1H, d, J=8.3 Hz), 4.07 (2H, s), 3.75 (4H, t, J=5.0 Hz), 2.73 (3H, s), 2.58 (4H, t, J=5.2 Hz), 2.39 (3H, s), m/z (ES$^+$) 491 (M+H)$^+$.

EXAMPLE 28

3-(5-Methyl-3-phenylisoxazol-4-yl)-8-(5-methylpyridin-2-yl)-5H-[1,2,4]triazolo[3,4-α]isoindole Prepared in a similar manner to Example 26 using 2-bromo-5-methylpyridine to give the title compound (33 mg, 35%).

¹H NMR (400 MHz, CDCl₃) δ 8.55–8.54 (2H, m), 8.13 (1H, dd, J=8.1, 1.6 Hz), 7.69 (1H, d, J=8.0 Hz), 7.63–7.61 (1H, m), 7.56–7.54 (2H, m), 7.47–7.34 (4H, m), 4.06 (2H, s), 2.72 (3H, s), 2.40 (3H, s).

EXAMPLE 29

Methyl-{6-[3-(-methyl-3-phenyl-isoxazol-4-yl)-5H-[1,2,4]triazolo[3,4-α]isoindol-8-yl]pyridin-2-yl}amine a) 8-(6-Bromopyridin-2-yl)-3-(5-methyl-3-phenylisoxazol-4-yl)-5H-[1,2,4]triazolo[3,4-α]isoindole Prepared in a similar manner to Example 26 using 2,6-dibromopyridine to give the title compound (480 mg, 44%). ¹H NMR (400 MHz, CDCl₃) δ 8.57 (1H, d, J=1.3 Hz), 8.16 (1H, dd, J=8.2, 1.8 Hz), 7.77–7.75 (1H, m), 7.68–7.64 (1H, m), 7.56–7.54 (2H, m), 7.49–7.36 (5H, m), 4.06 (2H, s), 2.73 (3H, s).

b) Methyl-{6-[3-(5-methyl-3-phenyl-isoxazol-4-yl)-5H-[1,2,4]triazolo[3,4-α]isoindol-8-yl]pyridin-2-yl}amine Prepared from 8-(6-bromopyridin-2-yl)-3-(5-methyl-3-phenylisoxazol-4-yl)-5H-[1,2,4]triazolo[3,4-α]isoindole in a similar manner to Example 24(b) to give the title compound (7 mg, 8%). ¹H NMR (400 MHz, CDCl₃) δ 8.63 (1H, d, J=1.3 Hz), 8.07 (1H, dd, J=8.0, 1.6 Hz), 7.56–7.38 (6H, m), 7.31 (1H, d, J=8.4 Hz), 7.07 (1H, d, J=7.3 Hz), 6.41 (1H, d, J=8.2 Hz), 4.64 (1H, brs), 4.05 (2H, s), 3.01 (3H, d, J=4.3 Hz), 2.72 (3H, s), m/z (ES⁺) 421 (M+H)⁺.

EXAMPLE 30

Dimethyl-{6-[3-(5-methyl-3-phenyl-isoxazol-4-yl)-5H-[1,2,4]triazolo[3,4-α]isoindol-8-yl]pyridin-2-ylmethyl}amine a) 2-Bromo-6-bromomethyl-pyridine A mixture of 2-bromo-6-methylpyridine (5.7 ml), NBS (8.9 g) and benzoyl peroxide (50 mg) in CCl₄ (50 ml) were heated to reflux for 16 h. The reaction was filtered and the solution obtained was used without further purification in the next step. ¹H NMR (400 MHz, CDCl₃) δ 7.56 (1H, t, J=7.8 Hz), 7.45–7.40 (1H, m), 7.28 (1H, d, J=8.2 Hz), 4.50 (2H, s).

b) (6-Bromopyridin-2-ylmethyl)dimethylamine

2-Bromo-6-bromomethyl-pyridine and NHMe₂ (10 ml of 2M solution in THF) were reacted at RT for 16 h. The reaction mixture was poured into H₂O, extracted into CH₂Cl₂ and the concentrated residue purified by column chromatography on silica, eluting with 1% MeOH/CH₂Cl₂ to give the title compound (440 mg). ¹H NMR (400 MHz, CDCl₃) δ 7.53 (1H, t, J=7.6 Hz), 7.40 (1H, d, J=7.5 Hz), 7.36 (1H, d, J=7.8 Hz), 3.57 (2H, s), 2.29 (6H, s).

c) Dimethyl-{6-[3-(5-methyl-3-phenyl-isoxazol-4-yl)-5H-[1,2,4]triazolo[3,4-α]isoindol-8-yl]pyridin-2-ylmethyl}amine Prepared in a similar manner to Example 26 using (6-bromopyridin-2-ylmethyl)-dimethylamine to give the title compound (40 mg, 39%). ¹H NMR (360 MHz, CDCl₃) δ 8.63 (1H, d, J=1.1 Hz), 8.13 (1H, dd, J=8.1, 1.5 Hz), 7.78 (1H, t, J=7.7 Hz), 7.67 (1H, d, J=7.7 Hz), 7.56–7.54 (2H, m), 7.47–7.34 (5H, m), 4.06 (2H, s), 3.70 (2H, s), 2.73 (3H, s), 2.37 (6H, s), m/z (ES⁺) 449 (M+H)⁺.

EXAMPLE 31

Methyl-{6-[3-(5-methyl-3-phenylisoxazol-4-yl)-5H-[1,2,4]triazolo[3,4-α]isoindol-8-yl]pyridin-2-ylmethyl}amine a) (6-Bromopyridin-2-ylmethyl)methylamine Prepared in a similar manner to Example 30(b) using NH₂Me (50 ml of 40% solution in water) to give the title compound (260 mg). ¹H NMR (400 MHz, d6 DMSO) δ 9.09 (1H, s), 7.87 (1H, t, J=7.8 Hz), 7.71 (1H, d, J=7.8 Hz), 7.58 (2H, d, J=7.7 Hz), 4.31 (2H, s), 2.63 (3H, s).

b) Methyl-{6-[3-(5-methyl-3-phenylisoxazol-4-yl)-5H-[1,2,4]triazolo[3,4-α]isoindol-8-yl]pyridin-2-ylmethyl}amine Prepared in a similar manner to Example 26 using (6-bromopyridin-2-ylmethyl)methylamine to give the title compound (15 mg, 15%). ¹H NMR (400 MHz, CDCl₃) δ 8.66 (1H, d, J=1.2 Hz), 8.13 (1H, dd, J=8, 1.6 Hz), 7.77 (1H, t, J=7.8 Hz), 7.67 (1H, d, J=7.7 Hz), 7.56–7.34 (6H, m), 7.30 (1H, d, J=7.5 Hz), 4.07 (2H, s), 3.97 (2H, s), 2.73 (3H, s), 2.57 (3H, s), m/z (ES⁺) 435 (M+H)⁺.

EXAMPLE 32

N,N,N'-Trimethyl-N'-{6-[3-(5-methyl-3-phenylisoxazol-4-yl)-5H-[1,2,4]triazolo[3,4-α]isoindol-8-yl]pyridin-2-ylmethyl} ethane-1,2-diamine a) N-(6-Bromopyridin-2-ylmethyl)-N,N',N'-trimethylethane-1,2-diamine Prepared in a similar manner to Example 30(b) using N,N,N'-trimethylethylenediamine (2.5 ml) to give the title compound (250 mg). ¹H NMR (360 MHz, CDCl₃) δ 7.52 (1H, t, J=7.6 Hz), 7.46 (1H, d, J=6.9 Hz), 7.35 (1H, d, J=7.6 Hz), 3.68 (2H, s), 2.58–2.55 (2H, m), 2.46–2.42 (2H, m), 2.30 (3H, s), 2.23 (6H, s).

b) N,N,N'-Trimethyl-N-{6-[3-(5-methyl-3-phenyl-isoxazol-4-yl)-5H-[1,2,4]triazolo[3,4-α]isoindol-8-yl]pyridin-2-ylmethyl} ethane-1,2-diamine Prepared in a similar manner to Example 26 using N-(6-Bromopyridin-2-ylmethyl)-N,N',N'-trimethylethane-1,2-diamine to give the title compound (6 mg, 5%).

¹H NMR (400 MHz, CD₃OD) δ 8.62 (1H, d, J=1.3 Hz), 8.17 (1H, dd, J=8.1, 1.6 Hz), 7.94–7.86 (2H, m), 7.56–7.44 (7H, m), 4.41 (2H, s), 3.85 (2H, s), 3.35–3.28 (4H, m), 2.66 (3H, s), 2.47 (6H, s), 2.40 (3H, s), m/z (ES⁺) 506 (M+H)⁺.

EXAMPLE 33

3-(5-Methyl-3-phenylisoxazol-4-yl)-9-(pyridin-3-yl)-5H-[1,2,4]triazolo[3,4-α]isoindole Prepared in a similar manner to Example 7 from 3-(5-methyl-3-phenylisoxazol-4-yl)-9-bromo-5H-[1,2,4]triazolo[3,4-a]isoindole (100 mg) (prepared using 7-bromo-2,3-dihydroisoindol-1-one by analogy with Example 4) and 3-bromopyridine (0.06 ml) to give the title compound (7 mg, 3%). ¹H NMR (360 MHz, CDCl₃) δ 8.90 (1H, s), 8.71 (1H, s), 8.40 (1H, d, J=5.8 Hz), 7.56–7.40 (8H, m), 7.30 (1H, d, J=7.3 Hz), 4.08 (2H, s), 2.68 (3H, s), miz (ES⁺) 392 (M+H)⁺.

EXAMPLE 34

3-(5-Methyl-3-phenylisoxazol-4-yl)-8-(pyridin-4-yl)-5H-[1,2,4]triazolo[3,4-α]isoindole A mixture of 8-bromo-3-(5-methyl-3-phenylisoxazol-4-yl)-5H-[1,2,4]triazolo[3,4-a]isoindole (220 mg) (prepared as in Example 4), 4-pyridylboranic acid (295 mg), $Cs_2CO_3$ (1.26 g/1 ml $H_2O$), and DME (3 ml) was degassed with a stream of $N_2$ for 0.5 h. Bis(triphenylphosphine)palladium(II) chloride (42 mg) was added and the reaction heated to 100° C. for 5 h. The reaction mixture was cooled, poured into $H_2O$ and extracted into $CH_2Cl_2$, dried ($MgSO_4$), and concentrated under reduced pressure. The residue was purified by column chromatography on silica, eluting with 3% $MeOH/CH_2Cl_2$, and recrystallised from $CH_2Cl_2$/hexane to give the title compound (50 mg, 21%). $^1H$ NMR (360 MHz, $CDCl_3$) δ 8.72 (2H, d, J=4.5 Hz), 8.29 (1H, d, J=1.3 Hz), 7.67 (1H, dd, J=8.0, 1.7 Hz), 7.57–7.53 (4H, m), 7.48–7.39 (4H, m), 4.07 (2H, s), 2.73 (3H, s), m/z (ES$^+$) 392 (M+H)$^+$.

EXAMPLE 35

3-[3-(5-Methyl-3-phenylisoxazol-4-yl-5H-[1,2,4]triazolo[3,4-α]isoindol-8-yl]-benzonitrile Prepared in a similar manner to Example 34 using 3-cyanophenylboronic acid to give the title compound (80 mg, 63%). $^1H$ NMR (400 MHz, $CDCl_3$) δ 8.22 (1H, s), 7.79–7.89 (2H, m), 7.71–7.59 (3H, m), 7.50–7.38 (6H, m), 4.07 (2H, s), 2.73 (3H, s), m/z (ES$^+$) 416 (M+H)$^+$.

EXAMPLE 36

8-Methyl-3-(5-methyl-3-phenylisoxazol-4-yl)-5H-[1,2,4]triazolo[3,4-α]isoindole A mixture of 8-bromo-3-(5-methyl-3-phenylisoxazol-4-yl)-5H-[1,2,4]triazolo[3,4-a]isoindole (100 mg) (prepared as in Example 4), methylboronic acid (72 mg), $K_3PO_4$ (276 mg), and dioxane (5 ml) was degassed with a stream of $N_2$ for 0.5 h. tetrakis(triphenylphosphine) palladium(0) (20 mg) was added and the reaction heated to 80° C. for 1 h. The reaction mixture was cooled, poured into $H_2O$ and extracted into $CH_2Cl_2$, dried ($MgSO_4$), and concentrated under reduced pressure to give the title compound (56 mg, 57%). $^1H$ NMR (400 MHz, $CDCl_3$) δ 7.82 (1H, s), 8.54–7.52 (2H, m), 7.47–7.37 (3H, m), 7.21 (1H, dd, J=7.8, 0.7 Hz), 7.14 (1H, d, J=8.0 Hz), 3.98 (2H, s), 2.70 (3H, s), 2.45 (3H, s), m/z (ES$^+$) 329 (M+H)$^+$.

EXAMPLE 37

3-(5-Methyl-3-phenylisoxazol-4-yl)-5H-[1,2,4]triazolo[3,4-α]isoindole-8-carbonitrile A mixture of 8-bromo-3-(5-methyl-3-phenylisoxazol-4-yl)-5H-[1,2,4]triazolo[3,4-a]isoindole (300 mg) (prepared as in Example 4), zinc cyanide (187 mg), and DMF (5 ml) was degassed with a stream of $N_2$ for 0.5 h. Tetrakis(triphenylphosphine) palladium(0) (20 mg) was added and the reaction heated to 80° C. for 2 days. The reaction mixture was cooled, poured into 10% ammonium hydroxide solution and extracted into EtOAc, dried ($MgSO_4$), and concentrated under reduced pressure. The residue was purified by column chromatography on silica, eluting with 50% EtOAc/hexane, and recrystallised from EtOAc/hexane to give the title compound (15 mg, 6%). $^1H$ NMR (360 MHz, $CDCl_3$) δ 8.28 (1H, s), 7.69 (1H, dd, J=8.0, 1.4 Hz), 7.54–7.50 (2H, m), 7.48–7.39 (4H, m), 4.05 (2H, s), 2.73 (3H, s), m/z (ES$^+$) 340 (M+H)$^+$.

EXAMPLE 38

8-Bromo-3-(5-hydroxymethylenyl-3-[4-fluorophenyl]isoxazol-4-yl)-5H-[1,2,4]triazolo[3,4-a]isoindole a) Methyl 5-methoxymethylene-3-[4-fluorophenyl]isoxazole 4-carboxylate Methyl 4-methoxyacetoacetate (24 ml) was added to a freshly prepared solution of sodium methoxide (1.2 eq) in 150 ml anhydrous methanol. The yellow solution was stirred for 30 minutes prior to dropwise addition of a solution of 4-fluorophenylchlorooxime in 50 ml anhydrous methanol. The reaction was allowed to stand overnight, filtered to remove solids and quenched with 5N HCl. The reaction was concentrated and partitioned between $CH_2Cl_2$—$H_2O$. The organic phase was dried ($MgSO_4$), concentrated and purified by dry flash chromatography using 5 then 10% EtOAc-isohexanes as eluent to give the title compound as a yellow solid (36 g, 95%).

$^1H$ NMR (400 MHz, $CDCl_3$) δ 7.66–7.62 (2H, m), 7.17–7.12 (2H, m), 4.87 (2H, s), 3.80 (3H, s), 3.52 (3H, s).

b) 4-Hydroxymethylene-5-methoxymethylene-3-[4-fluorophenyl]isoxazole

A suspension of methyl 5-methoxymethylene-3-[4-fluorophenyl]isoxazole 4-carboxylate (30 g, 0.113 mol) in 100 ml anhydrous toluene was cooled to –78° C. under nitrogen. Diisobutyl aluminium hydride (250 ml of 1.0 M solution in toluene) was added slowly and the reaction allowed to stir at –78° C. for 1.5 h. The reaction was quenched with methanol then partitioned between $CH_2Cl_2$—$H_2O$. The organic extracts were washed with brine, dried ($MgSO_4$), and concentrated to give the title compound as a yellow oil (14 g). $^1H$ NMR (400 MHz, $CDCl_3$) δ 7.79–7.75 (2H, m), 7.26–7.15 (2H, m), 4.67 (2H, s), 4.61–4.60 (2H, m), 3.50 (3H, s).

c) 5-Methoxymethylene-3-[4-fluorophenyl]isoxazole 4-carboxaldehyde

A suspension of Dess-Martin periodinane (8.26 g) in 50 ml $CH_2Cl_2$ was stirred at room temperature with 3 ml pyridine to give a turbid reaction. A solution of 4-hydroxymethylene-5-methoxymethylene-3-[4-fluorophenyl]isoxazole (4.2 g, 17.7 mmol) in 50 ml $CH_2Cl_2$ was added dropwise over 5 minutes and the reaction stirred for 30 minutes. The reaction was quenched with 1:1 $NaHCO_3$—$NaHSO_3$ and stirred for 1 h, extracted into $CH_2Cl_2$, washed with brine, dried ($MgSO_4$), and concentrated. Purification by chromatography using 20% EtOAc-isohexanes as eluent gave the title compound as a colourless solid (3.7 g, 89%). $^1H$ NMR (400 MHz, $CDCl_3$) δ 10.07 (1H, s), 7.77–7.73 (2H, m), 7.26–7.14 (2H, m), 4.90 (2H, s), 3.53 (3H, s).

d) 8-Bromo-3-(5-methoxymethylenyl-3-[4-fluorophenyl]isoxazol-4-yl)-5H-[1,2,4]triazolo[3,4-a]isoindole 5-Methoxymethylene-3-[4-fluorophenyl]isoxazole-4-carboxaldehyde (0.66 g) and (6-bromo-3H-isoindol-1-yl)hydrazine (0.64 g, 2.83 mmol) were reacted in a similar manner to that described in Example 4 to give the title compound (0.6 g). m/z (ES$^+$) 441/443 (M+H)$^+$ $^1$H NMR (400 MHz, d6-DMSO) δ 8.141–8.145 (1H, m), 7.703–7.708 (1H, m), 7.59–7.64 (3H, m), 7.27 (2H, m), 4.73–4.74(4H, m), 3.32 (3H, s).

e) 8-Bromo-3-(5-hydroxymethylenyl-3-[4-fluorophenyl]isoxazol-4-yl)-5H-[1,2,4]triazolo[3,4-a]isoindole A solution of 8-bromo-3-(5-methoxymethylenyl-3-[4-fluorophenyl]isoxazol-4-yl)-5H-[1,2,4]triazolo[3,4-a]isoindole (170 mg, 3.85 mmol) in 5 ml CH$_2$Cl$_2$ was cooled to –78° C. under a nitrogen atmosphere. Boron tribromide (250 µl) was added and the reaction allowed to attain room temperature. The reaction was re-cooled to 0° C. and quenched by addition of Et$_2$O followed by H$_2$O. The residue was concentrated and purified using dry flash column chromatography and CH$_2$Cl$_2$ then 3% MeOH—CH$_2$Cl$_2$ as eluent. The title compound was obtained after crystallisation from $^i$PrOH (135 mg, 82%). $^1$H NMR (400 MHz, d6-DMSO) δ 8.13 (1H, s), 7.70–7.72 (1H, m), 7.57–7.64 (3H, m), 7.27–7.32 (2H, m), 5.82 (1H, t, J=8.8 Hz), 4.80 (2H, s), 4.73–4.75 (2H, d, J=8.8 Hz). m/z (ES$^+$) 427/429 (M+H)$^+$.

EXAMPLE 39

8-Bromo-3-(5-chloro-3-phenylisoxazol-4-yl)-5H-[1,2,4]triazolo[3,4-a]isoindole

5-Chloro-3-phenylisoxazole 4-carboxaldehyde (1.1 g) and (6-bromo-3H-isoindol-1-yl)hydrazine (1.2 g, 5.3 mmol) were reacted in a similar manner to that described in Example 4 to give the title compound (415 mg, 19%). $^1$H NMR (400 MHz, d$_6$-DMSO) δ 8.161–8.165 (1H, m), 7.71–7.74 (1H, m), 7.47–7.61 (6H, m), 4.83 (2H, s).

EXAMPLE 40

8-Bromo-3-(5-[2-aminomethylpyridinyl)-3-phenyl-isoxazol-4-yl)-5H-[1,2,4]triazolo[3,4-a]isoindole 8-Bromo-3-(5-chloro-3-phenylisoxazol-4-yl)-5H-[1,2,4]triazolo[3,4-a]isoindole (50 mg, 0.12 mmol) (prepared in Example 39), sodium acetate (30 mg) and 2-(aminomethyl)pyridine (13 mg) in 5 ml methanol were heated to reflux for 18 h. The reaction was cooled, concentrated and partitioned between H$_2$O—CH$_2$Cl$_2$. The organic phase and extracts were combined, dried over (MgSO$_4$) and concentrated. The residue was purified by preparative TLC using 3% MeOH—CH$_2$Cl$_2$ as eluent. Trituration with $^i$PrOH gave the title compound as a beige solid (11 mg). $^1$H NMR (400 MHz, d6-DMSO) δ 8.53–8.54 (1H, m), 8.38–8.40 (1H, m), 8.1 (1H, s), 7.75–7.8 (1H, m), 7.65–7.68 (1H, m), 7.55–7.60 (2H, m), 7.38–7.5 (4H, m), 7.28–7.30 (2H, m), 4.68–4.7 (2H, m), 4.45 (2H, s). m/z (ES$^+$) 485/487 (M+H)$^+$.

EXAMPLE 41

3-(5-Methyl-3-phenyl-isoxazol-4-yl)-5H-[1,2,4]triazolo[3,4-a]isoindol-8-ylamine a) 1-(3-Phenyl-5-methyl-4-isoxazoloyl)-2-p-toluenesulfonylhydrazine 3-Phenyl-5-methyl-4-isoxazoyl hydrazide (40 g, 0.184 mol) (prepared as in Example 1) was dissolved in anhydrous pyridine (300 ml) and cooled to 0° C. p-Toluenesulfonyl chloride (35.15 g, 0.184 mol) was dissolved in anhydrous pyridine (200 ml) and added dropwise to the cooled hydrazide solution. The reaction was stirred for an additional 15 minutes at 0° C., warmed to 25° C., and the pyridine removed in vacuo. The residue was poured into 30% HCl and the product extracted into EtOAc. The organic layer was dried over MgSO$_4$ and evaporated. The residue was recrystallised from 70% EtOH to obtain the title compound as a beige solid (65 g, 95%). $^1$H NMR (360 MHz, CDCl$_3$) δ 7.75 (2H, d, J=2.2 Hz), 7.57–7.48 (5H, m), 7.29 (2H, d, J=2.2 Hz), 2.49 (3H, s), 2.43 (3H, s).

b) 4-(4-Methylphenylsulfonyl)hydrazono(chloro)methyl-5-methyl-3-phenylisoxazole 1-(3-phenyl-5-methyl-4-isoxazoloyl)-2-p-toluenesulfonyl-hydrazine (65 g, 0.175 mol) was placed in a flask containing thionyl chloride (300 ml) and the reaction heated to reflux under nitrogen for 2 h. The reaction mixture was cooled, the solvent removed in vacuo, and ethanol added to the residue. The resulting solid was filtered, washed with ethanol and dried in vacuo at 25° C. to obtain the title compound as a white solid (60 g, 88%). $^1$H NMR (400 MHz, CDCl$_3$) δ 8.25 (1H, s), 7.76–7.73 (2H, m), 7.46–7.29 (7H, m), 2.45 (3H, s), 2.42 (3H, s).

c) 6-Nitro-2,3-dihydro-isoindol-1-one

To a solution of 2,3-dihydroisoindole-1-one (5 g, 38 mmol) in concentrated sulfuric acid (100 ml) at 0° C., KNO$_3$ was added portionwise whilst maintaining the temperature at 0° C. The reaction was gradually allowed to warm to room temperature and was stirred overnight. The reaction mixture was poured into ice and the resulting precipitate was filtered off and dried to give title compound as a yellow solid (4.7 g, 70%). $^1$H NMR (360 MHz, d6 DMSO) δ 8.96 (1H, s), 8.45 (1H, dd, J=8.3 Hz, 2.2 Hz), 8.34 (1H, d, J=2 Hz), 7.87 (1H, d, J=8.3 Hz), 4.54 (2H, s). m/z (ES$^+$) 179 (M$^+$).

d) 6-Amino-2,3-dihydro-isoindol-1-one

6-Nitro-2,3-dihydro-isoindol-1-one (4.7 g, 26 mmol) was dissolved in acetic acid (130 ml) and hydrogenated at 50 psi (3 bar) in the presence of palladium on charcoal (0.47 g) overnight. The catalyst was filtered off through a pad of Hyflo™ and the acetic acid was removed in vacuo. The residue was triturated with dichloromethane/hexane and the resulting solid was filtered off to afford the title compound (3.56 g, 91%). $^1$H NMR (360 MHz, d6 DMSO) δ 8.28 (1H, s), 7.17 (1H, d, J=8 Hz), 6.82 (1H, s), 6.78 (1H, dd, J=8.1, 1.8 Hz), 5.25 (2H, s), 4.16 (2H, s). m/z (ES$^+$) 149 (M+H)$^+$.

e) (3-Oxo-2,3-dihydro-1H-isoindol-5-yl)carbamic acid tert-butyl ester

To a solution of 6-amino-2,3-dihydroisoindol-1-one (1.78 g, 12 mmol) in DMF/H$_2$O (2:1, 75 ml) was added K$_2$CO$_3$ (3.32 g, 24 mmol, 2 eq.) and di-tert-butyl dicarbonate (5.67 g, 26 mmol, 2.2 eq.). The reaction was stirred at room temperature overnight. The reaction was partitioned between ethyl acetate and water, and the organic layer was washed with saturated NaCl (aq), dried (MgSO$_4$), filtered and concentrated in vacuo. The residue was triturated with ethyl acetate and the resulting solid was filtered off to afford title compound (2.04 g, 68%). $^1$H NMR (360 MHz, d6 DMSO) δ 8.48 (1H, s), 7.83 (1H, d, J=1.2 Hz), 7.6 (1H, dd, J=8.2, 1.9 Hz), 7.43 (1H, d, J=8.2 Hz), 4.28 (2H, s), 1.49 (9H, s).

f) 5-tert-Butoxycarbonylamino-3-methoxy-1H-isoindolium trifluoromethane sulfonate Under nitrogen atmosphere, (3-oxo-2,3-dihydro-1H-isoindol-5-yl)-carbamic acid tert-butyl ester (2.14 g, 8.23 mmol)

was dissolved in dichloromethane (190 ml) and methyl triflate (1.40 ml, 12 mmol, 1.5 eq.) was added. The reaction was heated to reflux for 3 hours and then stirred at room temperature overnight. The reaction mixture was evaporated to one fifth of the original volume followed by the addition of diethyl ether. The resulting white precipitate was filtered off to afford the title compound title compound (2.71 g, 80%). $^1$H NMR (360 MHz, d6 DMSO) δ 9.87 (1H, s), 8.11 (1H, s), 7.75 (1H, d,J=1.9 Hz), 7.70 (1H, d, J=8.4 Hz), 4.93 (2H, s), 4.35 (3H, s), 1.50 (9H, s).

g) 3-(5-Methyl-3-phenylisoxazol-4-yl)-5H-[1,2,4]triazolo[3,4-a]isoindol-8-ylamine To a solution of 5-tert-butoxycarbonylamino-3-methoxy-1H-isoindolium trifluoromethane sulfonate (0.53 g, 1.29 mmol) in 1,4-dioxane was added N-p-toluenesulfonyl)-5-methyl-3-phenylisoxazol-4-hydrazidoyl chloride 4-(4-methylphenylsulfonyl)hydrazono(chloro)methyl-5-methyl-3-phenylisoxazole (0.5 g, 1.29 mmol) and triethylamine (0.18 ml, 1.29 mmol). The reaction was heated to reflux for one hour. The solvent was concentrated in vacuo and the residue was purified by silica chromatography, eluting with 2% methanol/dichloromethane. The resulting solid was dissolved in trifluoroacetic acid (5 ml) and was stirred at room temperature for 10 minutes. The reaction was concentrated in vacuo and the residue was partitioned between ethyl acetate and saturated K$_2$CO$_3$ (aq). The organic layer was washed with saturated NaCl (aq), dried (MgSO$_4$), filtered and concentrated in vacuo. The residue was purified by silica chromatography, eluting with ethyl acetate→3% methanol/ethyl acetate, to afford the title compound title compound (97 mg, 23%). $^1$H NMR (360 MHz, d6 DMSO) δ 7.53–7.44 (5H, m), 7.17 (1H, d, J=8.4 Hz), 7.14 (1H, s), 6.74 (1H, d, J=7.9 Hz), 4.33 (2H, s), 2.59 (3H, s). m/z (ES$^+$) 330 (M+H)$^+$.

EXAMPLE 42

3-(5-Methyl-3-phenylisoxazol-4-yl)-8-(pyridin-3-ylmethoxy)-5H-[1,2,4]triazolo[3,4-α]isoindole Under nitrogen atmosphere, triphenylphosphine bound resin (0.41 g, 0.45 mmol, 1.12 mmol/g) was swelled in dichloromethane for 30 minutes. 3-(5-Methyl-3-phenylisoxazol-4-yl)-5H-[1,2,4]triazolo[3,4-a]isoindol-8-ol (0.1 g, 0.30 mmol) (prepared by Example 3 step (a)), 3-hydroxymethylpyridine (44 μl, 0.45 mmol, 1.5 eq.) and diethyl azodicarboxylate (71 μl, 0.45 mmol, 1.5 eq.) were added and the reaction was stirred at room temperature overnight. The resin was filtered off and washed with dichloromethane, methanol and diethyl ether. The combined organics were concentrated in vacuo. The residue was purified firstly by alumina chromatography, eluting with 1% methanol/dichloromethane, and secondly by silica chromatography, using dichloromethane→5% methanol/dichloromethane as the eluant, to afford the title compound (21 mg, 16%). $^1$H NMR (400 MHz, CDCl$_3$) δ 8.70–8.69 (1H, m), 8.61–8.59 (1H, m), 7.80 (1H, dt, J=7.8, 2.1 Hz), 7.59 (1H, d, J=2.4 Hz), 7.54–7.52 (2H, m), 7.46–7.33 (4H, m), 7.18 (1H, d, J=8.4 Hz), 7.02 (1H, dd, J=8.4, 2.4 Hz), 5.16 (2H, s), 3.96 (2H, s), 2.70 (3H, s). m/z (ES$^+$) 422 (M+H)$^+$.

EXAMPLE 43

3-(5-Methyl-3-phenylisoxazol-4-yl)-8-(pyridin-2-ylmethoxy)-5H-[1,2,4]triazolo[3,4-α]isoindole Prepared in a similar manner to Example 42 using 2-hydroxymethylpyridine to yield the title compound (40 mg, 10%). $^1$H NMR (400 MHz, CDCl$_3$) δ 8.62 (1H, dd, J=2.6, 2.3 Hz), 7.73 (1H, td, J=7.7, 1.7 Hz), 7.60 (1H, d, J=2.4 Hz) 7.54–7.38 (6H, m), 7.25–7.24 (1H, m), 7.16 (1H, d, J=8.6 Hz), 7.05 (1H, dd, J=8.5, 2.4 Hz), 5.27 (2H, s), 3.95 (2H, s), 2.70 (3H, s). m/z (ES$^+$) 422 (M+H)$^+$.

EXAMPLE 44

3-(5-Methyl-3-phenylisoxazol-4-yl)-8-(piperidin-4-yloxy)-5H-[1,2,4]triazolo[3,4-α]isoindole a) 4-[3-(5-Methyl-3-phenylisoxazol-4-yl)-5H-[1,2,4]triazolo[3,4-α]isoindol-8-yloxy]-piperidine-1-carboxylic acid tert-butyl ester Under nitrogen atmosphere, triphenylphosphine bound resin (1.22 g, 1.36 mmol, 1.12 mmol/g) was swelled in dichloromethane for 30 minutes. 3-(5-Methyl-3-phenylisoxazol-4-yl)-5H-[1,2,4]triazolo[3,4-a]isoindol-8-ol (0.3 g, 0.91 mmol) (prepared as in Example 3, Step (a)), 4-hydroxy-boc-piperidine (0.27 g, 1.36 mmol, 1.5 eq.) and diethyl azodicarboxylate (0.21 ml, 1.36 mmol, 1.5 eq.) were added and the reaction was stirred at room temperature overnight. The resin was filtered off and washed with dichloromethane, methanol and ether. The combined organics were concentrated in vacuo. The residue was purified by alumina chromatography, eluting with dichloromethane 2% methanol/dichloromethane (0.5% methanol gradient), and was used without further purification in the next step.

b) 3-(5-Methyl-3-phenylisoxazol-4-yl)-8-(piperidin-4-yloxy)-5H-[1,2,4]triazolo[3,4-α]isoindole 4-[3-(5-Methyl-3-phenylisoxazol-4-yl)-5H-[1,2,4]triazolo[3,4-α]isoindol-8-yloxy]-piperidine-1-carboxylic acid tert-butyl ester (466 mg, 0.91 mmol) was dissolved in TFA (5 ml) and stirred at room temperature for 1 hour. The reaction was concentrated in vacuo and the residue was partitioned between ethyl acetate and saturated K$_2$CO$_3$ (aq). The organic layer was dried (MgSO$_4$), filtered and concentrated in vacuo. The residue was purified by alumina chromatography, eluting with dichloromethane→5% methanol/dichloromethane (in 1% methanol gradient), to afford the title compound as a white solid (4 mg, 1% over 2 steps). $^1$H NMR (400 MHz, d4 MeOH) δ 7.53–7.43 (6H, m), 7.32 (1H, d, J=8.5 Hz), 7.08 (1H, dd, J=8.5, 2.4 Hz), 4.63–4.60 (1H, m), 4.24 (2H, s), 3.16–3.11 (2H, m), 2.85–2.79 (2H, m), 2.64 (3H, s), 2.09–2.05 (2H, m), 1.78–1.72 (2H, m). m/z (ES$^+$) 414 (M+H)$^+$.

EXAMPLE 45

3-(5-Methyl-3-phenylisoxazol-4-yl)-8-(1-methyl-1,2,3,6-tetrahydropyridin-4-yl)-5H-[1,2,4]triazolo[3,4-α]isoindole a) 4-Tributylstannyl-3,6-dihydro-2H-pyridine-1-carboxylic acid tert-butyl ester Prepared according to WO-A-0123381.

b) 4-[3-(5-Methyl-3-phenylisoxazol-4-yl)-5H-[1,2,4]triazolo[3,4-α]isoindol-8-yl]-3,6-dihydro-2H-pyridine-1-carboxylic acid tert-butyl ester 8-Iodo-3-(5-methyl-3-phenylisoxazol-4-yl)-5H-[1,2,4]triazolo[3,4-a]isoindole (837 mg, 1.9 mmol) (as prepared in Example 6 Step (d)) and 4-tributylstannyl-3,6-dihydro-2H- pyridine-1-carboxylic acid tert-butyl ester (1.35 g, 2.85 mmol, 1.5 eq.) were dissolved in DMF (40 ml) and degassed with nitrogen for one hour.

Pd(PPh$_3$)$_2$Cl$_2$ (33 mg, 0.05 mmol) was added and the reaction was heated to 100° C. for 8 hours. The reaction was partitioned between ethyl acetate and water. The organic layer was washed with water (×3) and saturated NaCl (aq), dried (MgSO$_4$), filtered and concentrated in vacuo. The residue was purified by silica chromatography, eluting with 70% ethyl acetate/hexane→ethyl acetate, to afford the title compound (750 mg, 80%). $^1$H NMR (360 MHz, CDCl$_3$) δ 8.01 (1H, s), 7.54–7.52 (2H, m), 7.46–7.40 (4H, m), 7.23 (1H, d, J=8.1 Hz), 6.25–6.23 (1H, m), 4.13–4.11 (2H, m), 4.01 (2H, s), 3.66 (2H, t), 2.71 (3H, s), 2.56–2.54 (2H, m), 1.50 (9H, s). m/z (ES$^+$) 496 (M+H)$^+$.

c) 3-(5-Methyl-3-phenylisoxazol-4-yl)-8-(1,2,3,6-tetrahydropyridin-4-yl)-5H-[1,2,4]triazolo[3,4-α]isoindole 4-[3-(5-Methyl-3-phenylisoxazol-4-yl)-5H-[1,2,4]triazolo[3,4-α]isoindol-8-yl]-3,6-dihydro-2H-pyridine-1-carboxylic acid tert-butyl ester (750 mg, 1.52 mmol) was dissolved in TFA (10 ml) and stirred at room temperature for 30 minutes. The reaction was concentrated in vacuo and the residue was partitioned between ethyl acetate and saturated K$_2$CO$_3$ (aq). The organic layer was dried (MgSO$_4$), filtered, concentrated in vacuo. The residue was purified by alumina chromatography, using dichloromethane→5% methanol/dichloromethane (in 1% methanol gradient) as the eluant, to yield the title compound (460 mg, 77%). $^1$H NMR (360 MHz, CDCl$_3$) δ 8.02 (1H, d, J=1.04 Hz), 7.54–7.52 (2H, m), 7.47–7.38 (4H, m), 7.21 (1H, d, J=8.1 Hz), 6.23 (1H, t), 4.00 (2H, s), 3.59–3.58 (2H, m), 3.16 (2H, m), 2.71 (3H, s), 2.52–2.50 (2H, m). m/z (ES) 396 (M+H)$^+$.

d) 3-(5-Methyl-3-phenylisoxazol-4-yl)-8-(1-methyl-1,2,3,6-tetrahydropyridin-4-yl)-5H-[1,2,4]triazolo[3,4-α]isoindole Under nitrogen atmosphere, 3-(5-Methyl-3-phenylisoxazol-4-yl)-8-(1,2,3,6-tetrahydropyridin-4-yl)-5H-[1,2,4]triazolo[3,4-α]isoindole (50 mg, 0.13 mmol) was dissolved in methanol (2 ml) and formalin solution (65 μl, 0.8 mmol) and sodium cyanoborohydride (32 mg, 0.52 mmol) were added. The reaction was stirred at room temperature for 3 hours. The reaction was concentrated in vacuo and partitioned between ethyl acetate and water. The organic layer was washed with saturated NaCl (aq), dried (MgSO$_4$), filtered and concentrated in vacuo. The residue was purified by alumina chromatography eluting with dichloromethane→2% methanol/dichloromethane (in 0.5% methanol gradient) to yield the title compound (21 mg, 41%). $^1$H NMR (400 MHz, d4 McOH) δ 8.01 (1H, d, J=1.3 Hz), 7.59 (1H, dd, J=1.6, 8.2 Hz), 7.52–7.42 (5H, m), 7.40 (1H, d, J=8.2 Hz), 6.28–6.27 (1H m), 4.31 (2H, s), 3.21–3.20 (2H, m), 2.78 (2H, m), 2.69–2.66 (2H, m), 2.64 (3H, s), 2.43 (3H, s).

EXAMPLE 46

6-[3-(5-Methyl-3-phenylisoxazol-4-yl)-5H-[1,2,4]triazolo[3,4-a]isoindol-8-yl]pyrazine-2-carboxylic acid A mixture of 8-(5,5-dimethyl-[1,3,2]dioxaborinan-2-yl)-3-(5-methyl-3-phenylisoxazol-4-yl)-5H-[1,2,4]triazolo[3,4-α]isoindole (248 mg, 0.58 mmol) (as prepared in Example 26 Step (a)), methyl 6-chloropyrazine-2-carboxylate (100 mg, 0.58 mmol), dioxane (4.8 ml) and 2M aqueous Cs$_2$CO$_3$ solution (0.58 ml) was degassed with a stream of N$_2$ for 10 min. Bis(triphenylphosphine)palladium dichloride (12 mg, 0.22 μmol) was added and the stirred mixture was heated at reflux for 1.5 h. The reaction was then cooled, allowed to stand for 15 min and the supernatant decanted off. The remaining salts were washed with further dioxane (5 ml) and then partitioned between water (20 ml) and CH$_2$Cl$_2$ (20 ml). The pH was adjusted to 6 by dropwise addition of 2N aqueous HCl and the aqueous phase was extracted with further CH$_2$Cl$_2$ (2×20 ml). The combined organic extracts were dried over Na$_2$SO$_4$ and concentrated in vacuo to yield the title compound as a white amorphous solid (89.8 mg, 34%); $^1$H NMR (400 MHz, CDCl$_3$) δ 9.63 (1H, s), 9.19 (1H, s), 8.81 (1H, s), 8.38 (1H, dd, J=8.2, 1.7 Hz), 7.75 (1H, d, J=8.2 Hz), 7.56–7.48 (5H, m), 4.67 (2H, s), 2.64 (3H, s); m/z (ES$^+$) 437 (M+H)$^+$.

EXAMPLE 47

8-Bromo-3-(5-fluoromethylenyl-3-[4-fluorophenyl]isoxazol-4-yl)-5H-[1,2;4]triazolo[3,4-a]isoindole A suspension of 8-bromo-3-(5-hydroxymethylenyl-3-[4-fluorophenyl]isoxazol-4-yl)-5H-[1,2,4]triazolo[3,4-a]isoindole (93 mg, 0.21 mmol) (prepared as in Example 38) in 3 ml CH$_2$Cl$_2$ was cooled to −78° C. under a N$_2$ atmosphere. (Diethylaminosulphur) trifluoride (60 μL) was added and the reaction allowed to warm to 0° C. after 20 minutes. The reaction was poured into water, extracted, dried over MgSO$_4$ and concentrated. The residue was purified by preparative tlc using 1% MeOH—CH$_2$Cl$_2$ as eluent. The title compound was obtained as a solid (2 mg). $^1$H NMR (400 MHz, d6-DMSO) δ 8.14 (1H, s), 7.57–7.72 (4H, m), 7.31–7.35 (2H, m), 7.75 (2H, m), 4.69 (2H, s). m/z (ES$^+$) 429/431 (M+H)$^+$.

EXAMPLE 48

3-(5-Methyl-3-phenylisoxazol-4-yl)-8-(pyridin-3-yl)-5H-[1,2,4]triazolo[3,4-α]isoindole A mixture of 8-bromo-3-(5-methyl-3-phenylisoxazol-4-yl)-5H-[1,2,4]triazolo[3,4-a]isoindole (100 mg) (as prepared in Example 4), 3-(tri-n-butylstannyl)pyridine (442 mg) and DMF (5 ml) was degassed with a stream of N$_2$ for 0.5 h. Bis(triphenylphosphine)palladium(II) chloride (5 mg) was added and the reaction heated to 100° C. for 2 h. The mixture was concentrated under reduced pressure and the residue purified by column chromatography on silica, eluting with 2.5% MeOH/CH$_2$Cl$_2$ to give the title compound (75 mg, 64%). $^1$H NMR (400 MHz, CDCl$_3$) δ 8.66 (1H, t, J=3.3 Hz), 8.23 (1H, d, J=1.4 Hz), 7.95–7.92 (1H, m), 7.63 (1H, dd, J=8.0, 1.7 Hz), 7.57–7.54 (2H, m), 7.49–7.38 (5H, m), 4.07 (2H, s), 3.97 (2H, s), 2.73 (3H, s), m/z (ES$^+$) 392 (M+H)$^+$.

The invention claimed is:

1. A compound of formula 1:

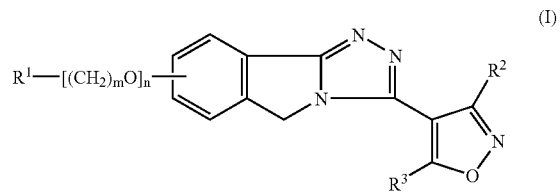

in which:
- $R^1$ is hydrogen, halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy $C_{1-6}$alkyl, $C_{1-6}$alkoxy$C_{1-6}$alkyl, amino$C_{1-6}$alkyl or $C_{1-6}$alkylcarbonyl each of which is unsubstituted or substituted by one, two or three halogen atoms;
- $R^2$ is phenyl, which is unsubstituted or substituted with at least one group selected from halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy$C_{1-6}$alkyl, $C_{1-6}$alkoxy$C_{1-6}$alkyl, amino$C_{1-6}$alkyl or $C_{1-6}$alkylcarbonyl each of which is itself unsubstituted or substituted by one, two or three halogen atoms;
- $R^3$ is hydrogen, halogen, cyano, amino, nitro, hydroxy, aminocarbonyl, $C_{1-6}$alkyl, $C_{2-6}$alkenyl, $C_{2-6}$alkynyl, $C_{1-6}$alkoxy, $C_{2-6}$alkenyloxy, $C_2$alkynyloxy, hydroxy $C_{1-6}$alkyl, $C_{1-6}$alkoxy$C_{1-6}$alkyl, amino$C_{1-6}$alkyl, $C_{1-6}$alkylcarbonyl or $NR^cR^d$, each of which is unsubstituted or substituted by one, two or three halogen atoms;
- $R^a$ and $R^b$ are each independently hydrogen, $C_{1-6}$alkyl, $C_{1-6}$alkoxy, $C_{2-6}$alkenyl, $C_{2-6}$alkynyl, amino$C_{1-6}$alkyl or phenyl;
- $R^c$ and $R^d$ are each independently hydrogen, $C_{1-6}$alkyl, $C_{1-6}$alkoxy, $C_{2-6}$alkenyl or $C_{2-6}$alkynyl;
- m is 0, 1, 2 or 3; and
- n is 0 or 1;

or a pharmaceutically acceptable salt thereof.

2. A compound of claim 1 in which $R^1$ is hydrogen, halogen, hydroxy, cyano, nitro, $C_{1-4}$alkyl, $C_{1-4}$alkoxy or halogenated $C_{1-4}$alkoxy.

3. A compound of claim 1 in which $R^3$ represents a halogen, $C_{1-4}$alkyl, hydroxy $C_{1-4}$alkyl, halogenated $C_{1-4}$alkyl or $NR^cR^d$ group, in which $R^c$ and $R^d$ are as defined in claim 1.

4. A compound of claim 1 in which:
- n represents 0 and $R^1$ represents hydrogen, cyano, amino, bromo, methyl, methoxy; or
- n represents 1, m represents 2 and $R^1$ represents pyridinyl;
- $R^2$ represents phenyl or fluorophenyl;
- $R^3$ represents chloro, methyl, hydroxymethyl, fluoromethyl or

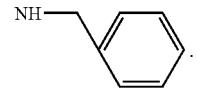

5. A compound of claim 1 which is:
- 3-(5-methyl-3-phenylisoxazol-4-yl)-5H-[1,2,4]triazolo[3,4-α]isoindole;
- 8-methoxy-3-(5-methyl-3-phenylisoxazol-4-yl)-5H-[1,2,4]triazolo[3,4-a]isoindole;
- 8-bromo-3-(5-methyl-3-phenylisoxazol-4-yl)-5H -[1,2,4]triazolo[3,4-a]isoindole;
- 6-bromo-3-(5-methyl-3-phenylisoxazol-4-yl)-5H -[1,2,4]triazolo[3,4-a]isoindole; 8-Methyl-3-(5-methyl-3-phenylisoxazol-4-yl)-5H-[1,2,4]triazolo[3,4-α]isoindole;
- 3-(5-methyl-3-phenylisoxazol-4-yl)-5H-[1,2,4]triazolol[3,4-α]isoindole-8-carbonitrile;
- 8-Bromo-3-(5-hydroxymethylenyl-3-[4-fluorophenyl]isoxazol-4-yl)-5H-[1,2,4]triazolo[3,4-α]isoindole;
- 8-Bromo-3-(5-chloro -3-phenylisoxazol-4-yl)-5H-[1,2,4]triazolo[3,4-α]isoindole;
- 3-(5-methyl-3-phenyl-isoxazol-4-yl)-5H-[1,2,4]triazolo[3,4-α]isoindol-8-ylamine;
- 8-Bromo-3-(5-fluoromethylenyl-3-[4-fluorophenyl]isoxazol-4-yl)-5H-[1,2,4]triazolo[3,4-α]isoindole;

or a pharmaceutically acceptable salt thereof.

6. A pharmaceutical composition comprising an effective amount of a compound of claim 1 or a pharmaceutically acceptable salt thereof and a pharmaceutically acceptable carrier.

7. A compound of claim 1 in which $R^1$ is hydrogen, bromo, nitro, cyano, hydroxy, methyl, methoxy or trifluoromethoxy.

* * * * *